(12) United States Patent
Tcheng et al.

(10) Patent No.: US 9,126,042 B2
(45) Date of Patent: Sep. 8, 2015

(54) RESPONSIVE ELECTRICAL STIMULATION FOR MOVEMENT DISORDERS

(71) Applicant: NeuroPace, Inc., Mountain View, CA (US)

(72) Inventors: Thomas K. Tcheng, Pleasant Hill, CA (US); Robert E. Fischell, Dayton, MD (US); Benjamin D. Pless, Atherton, CA (US)

(73) Assignee: NeuroPace, Inc., Mountain View, CA (US)

( * ) Notice: Subject to any disclaimer, the term of this patent is extended or adjusted under 35 U.S.C. 154(b) by 0 days.

(21) Appl. No.: 14/484,701

(22) Filed: Sep. 12, 2014

(65) Prior Publication Data

US 2014/0379046 A1 Dec. 25, 2014

Related U.S. Application Data

(60) Division of application No. 14/059,090, filed on Oct. 21, 2013, which is a continuation of application No. 12/881,143, filed on Sep. 13, 2010, now Pat. No. 8,594,795, which is a continuation of application No. 11/517,783, filed on Sep. 8, 2006, now Pat. No. 7,813,802, which is a continuation of application No. 10/072,669, filed on Feb. 5, 2002, now Pat. No. 7,110,820.

(51) Int. Cl.
*A61N 1/00* (2006.01)
*A61N 1/36* (2006.01)

(52) U.S. Cl.
CPC ........ *A61N 1/36067* (2013.01); *A61N 1/36135* (2013.01)

(58) Field of Classification Search
CPC ............ A61N 1/3605; A61N 1/36064; A61N 1/36067; A61N 1/36053
USPC ............................... 607/45, 62; 600/544–546
See application file for complete search history.

(56) References Cited

U.S. PATENT DOCUMENTS

| | | |
|---|---|---|
| 5,040,535 A | 8/1991 | Mann et al. |
| 5,335,657 A | 8/1994 | Terry et al. |
| 5,683,422 A | 11/1997 | Rise |
| 5,707,396 A | 1/1998 | Benabid |
| 5,716,377 A | 2/1998 | Rise et al. |
| 5,735,887 A | 4/1998 | Barreras, Sr. et al. |
| 5,792,186 A | 8/1998 | Rise |
| 5,995,868 A | 11/1999 | Dorfmeister et al. |

(Continued)

OTHER PUBLICATIONS

Dilorenzo, "Optimal Method and Apparatus for Neural Modulation for the Treatment of Neurologic Disease, Particularly Movement Disorders", U.S. Appl. No. 60/095,413, filed Aug. 5, 1998.

(Continued)

*Primary Examiner* — Scott Getzow
(74) *Attorney, Agent, or Firm* — Arent Fox LLP

(57) ABSTRACT

An implantable neurostimulator system for treating movement disorders includes a sensor, a detection subsystem capable of identifying episodes of a movement disorder by analyzing a signal received from the sensor, and a therapy subsystem capable of supplying therapeutic electrical stimulation to treat the movement disorder. The system treats movement disorders by detecting physiological conditions characteristic of an episode of symptoms of the movement disorder and selectively initiating therapy when such conditions are detected.

18 Claims, 18 Drawing Sheets

(56) References Cited

U.S. PATENT DOCUMENTS

| | | |
|---|---|---|
| 6,006,124 A | 12/1999 | Fischell et al. |
| 6,016,449 A | 1/2000 | Fischell et al. |
| 6,066,163 A | 5/2000 | John |
| 6,128,538 A | 10/2000 | Fischell et al. |
| 6,134,474 A | 10/2000 | Fischell et al. |
| 6,227,203 B1 | 5/2001 | Rise et al. |
| 6,253,109 B1 | 6/2001 | Gielen |
| 6,353,754 B1 | 3/2002 | Fischell et al. |
| 6,356,784 B1 | 3/2002 | Lozano et al. |
| 6,360,122 B1 | 3/2002 | Fischell et al. |
| 6,366,813 B1 | 4/2002 | DiLorenzo |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,480,743 B1 | 11/2002 | Kirkpatrick et al. |
| 6,484,059 B2 | 11/2002 | Gielen |
| 6,591,138 B1 | 7/2003 | Fischell et al. |
| 6,622,038 B2 | 9/2003 | Barrett et al. |
| 6,647,296 B2 | 11/2003 | Fischell et al. |
| 6,690,974 B2 | 2/2004 | Archer et al. |
| 6,810,285 B2 | 10/2004 | Pless et al. |
| 6,923,784 B2 | 8/2005 | Stein |
| 6,944,501 B1 | 9/2005 | Pless |
| 7,110,820 B2 | 9/2006 | Tcheng et al. |
| 7,813,802 B2 | 10/2010 | Tcheng et al. |
| 2002/0038137 A1 | 3/2002 | Stein |

OTHER PUBLICATIONS

Benabid et al., "Long-Term Electrical Inhibition of Deep Brain Targets in Movement Disorders", Movement Disorders 1998; 13 (Supp. 3) 119-125.

Gross et al., "Advances in Neurostimulation for Movement Disorders", Neurological Research 2000, 22: 247-258.

Cooper et al., "Chronic Cerebellar Stimulation (CCS) and Deep Brain Stimulation (DBS) in Involuntary Movement Disorders", Applied Neurophysiology 1982, 45(3); 209-17.

Blond et al., "Control of Tremor and Involuntary Movement Disorders by Chronic Stereotactic Stimulation of the Ventral Intermediate Thalamic Nucleus", J. neurosurgery 1992.

RESPONSIVE ELECTRICAL STIMULATION FOR MOVEMENT DISORDERS

CROSS-REFERENCE TO RELATED APPLICATION

This is a divisional of U.S. Ser. No. 14/059,090, filed Oct. 21, 2013, which is a continuation of U.S. Ser. No. 12/881,143, filed Sep. 13, 2010, now U.S. Pat. No. 8,594,795, which is a continuation of U.S. Ser. No. 11/517,783, filed Sep. 8, 2006, now U.S. Pat. No. 7,813,802, which is a continuation of U.S. Ser. No. 10/072,669, filed Feb. 2, 2002, now U.S. Pat. No. 7,110,820, each of which is hereby incorporated by reference in its entirety.

FIELD OF THE INVENTION

The invention relates to systems and methods for applying responsive electrical stimulation for treating movement disorders, and more particularly to systems and methods employing an implantable responsive neurostimulator to deliver electrical stimulation therapy in response to detected physiological conditions, either alone or in combination with other therapies.

BACKGROUND OF THE INVENTION

Movement disorders, i.e. neurological diseases or other problems that result in movement or muscle control problems are debilitating to a great number of individuals worldwide. In general, various movement disorders are characterized by uncontrolled or poorly controlled movement, involuntary movement, an inability or reduced ability to move, or improper muscle tone.

Parkinson's Disease is generally characterized by tremor, an involuntary movement of the limbs and extremities that leads to an inability to perform normal daily life activities. It is believed that the symptoms of Parkinson's Disease are caused at least in part by a loss of dopaminergic neurons in the substantia nigra, a brain structure with an inhibitory effect on movement. Other symptoms of Parkinson's Disease include rigidity (undesired increased muscle tone, often leading to a "locking" effect in the limbs) and bradykinesia (slower-than-desired movements, and difficulty in initiating movements).

Essential Tremor, as its name suggests, is also characterized primarily by tremor in the limbs and extremities. Tremor can also result as a symptom of Multiple Sclerosis and other diseases and disorders.

Other movement disorders are characterized by different symptoms. Dyskinesias, such as Huntington's Chorea, result in other forms of unwanted movement. Huntington's Chorea, in particular, is a congenital disorder that causes undesired "dance-like" movements of the limbs. It is believed to be caused by degeneration of the striatum. Hemiballismus, another dyskinesia, causes flailing of the limbs on one side of the body and is believed to be caused by degeneration of the subthalamic nucleus.

While drug therapy provides good results for a substantial number of patients suffering from various movement disorders, particularly in the early stages before the disorders have progressed, there are some disadvantages to using drugs. In particular, patient compliance is particularly difficult to achieve when complex drug regimens are necessary to maintain an effective serum concentration. If drug levels are too low, the therapy may be ineffective; high levels can be damaging—they may cause serious side effects or even exacerbate the patient's movement disorders.

Surgery has also shown some promise and is effective with some patients, especially since there are fewer ongoing patient compliance issues (although patients who have had resective brain surgery are frequently kept on drug therapy as well). For example, lesions can be produced in the thalamus, globus pallidus, and other brain structures in an attempt to regulate patients' symptoms. However, clearly, resective brain surgery is irreversible and risky—neurological deficits have been known to occur.

Accordingly, described herein are two types of disorders of the human brain that have been shown to be effectively treated by the use of electrical stimulation. A first type of disorder is involuntary motion disorders such as the tremor associated with Parkinson's disease, familial tremor, tics or any other disorder that results in a shaking of a patient's hand, head or any other body part. A second type of disorder is associated with loss of muscular control as for example dystonia, spasticity or rigidity.

Continuous deep brain stimulation, particularly in the ventralis intermedius (Vim) nucleus of the thalamus, also has been shown to provide some relief from the symptoms of various movement disorders. However, this approach has resulted in some unpleasant side effects, in particular paresthesias, numbness, and slurring of speech. Moreover, a relatively small implantable device capable of performing continuous stimulation would tend to have a shorter battery life than would be desirable. Unlike other surgical treatments, continuous deep brain stimulation is reversible, in the event the side effects or neurological deficits resulting therefrom are more debilitating or unpleasant than the movement disorder. See, e.g., A. L. Benabid et al., "Long-Term Electrical Inhibition of Deep Brain Targets in Movement Disorders," Movement Disorders 1998, 13 (Supp. 3): 119-25; and R. E. Gross et al., "Advances in Neurostimulation for Movement Disorders," Neurological Research 2000, 22: 247-258.

Deep brain recordings from patients with tremor have shown an abnormal rhythmic electrical activity in the thalamus, globus pallidus, and subthalamic nucleus at a frequency of approximately 3-5 Hz. This rhythmic activity is associated with tremor, i.e., there is a substantially constant frequency and phase relationship between tremor and the electrophysiological activity. When electrical stimulation is applied in this same region of the brain where the 3-5 Hz signal is detected, the involuntary motion can be eliminated or at least moderated. Applying an electrical signal at 30-180 Hz using 300 microsecond biphasic pulses has been shown to eliminate or attenuate tremor. Stimulation by deep brain electrodes at 60-70 Hz using 300 microsecond biphasic pulses at 3-6 volts has been shown to cause a reduction in spasticity thereby allowing more normal movements.

Even voluntary and intentional movement causes observable signals in the thalamus; tremor is manifested by regular oscillations at a patient-specific frequency. It is of course understood that other regimens of electrical stimulation can also be used for treating involuntary motion and muscle tone disorders.

Both the detection of abnormal deep brain electrical signals and the control of abnormal motion and motor control disorders have been reported by Cooper, Upton and Amin. See I. S. Cooper et al., "Chronic Cerebellar Stimulation (CCS) and Deep Brain Stimulation (DBS) in involuntary movement disorders," Applied Neurophysiology 1982, 45(3): 209-17. There is no currently available device that can provide either or both responsive and/or continuous electrical stimulation via deep brain electrodes to reduce or eliminate involuntary motion disorders and/or muscle tone disorders. The Medtronic Activa implantable pulse generator is now in use for Parkinson's disease. The Activa provides periodic or continuous stimulation to the thalamus through deep brain electrodes but has no responsive capabilities. In U.S. Pat. No. 6,016,449, Fischell et al. describe a sophisticated cranially implanted neurostimulator with responsive electrical stimulation capabilities, generally described as being used in the treatment of epilepsy.

SUMMARY OF THE INVENTION

The invention is a responsive system, at least part of which is an implantable neurostimulator, suited to be implanted within a human patient, for decreasing involuntary motion tremor and other symptoms associated with Parkinson's disease and other diseases of the brain that tend to cause abnormal movements or inappropriate muscle tone. The implanted neurostimulator of the present invention can also generate either or both continuous and/or responsive stimulation to treat muscle tone disorders that include (but are not limited to) dystonia, spasticity, and rigidity.

The implanted portion of the system generally includes an electrode array that is placed deep within the patient's brain. For one embodiment, a control module is placed into a section of the cranium where cranial bone has been removed. The control module is electrically connected to deep brain electrodes by means of leads that run beneath the patient's scalp or within the patient's cranium. A typical location for the electrodes would be in the vicinity of the thalamus, the internal capsule, or the basal ganglia (particularly the Globus Pallidus Internus and the Subthalamic Nucleus).

As explained above, it has been shown that prior to a visible tremor being experienced by (for example) a Parkinson's disease patient, there is likely to be a detectable electrical signal correlated with the tremor that is detectable in the vicinity of the thalamus. This signal generally starts at a low amplitude that does not cause an observable clinical tremor. Over a period of a few seconds, the amplitude continues to increase. When the amplitude reaches a certain level, the patient will begin to show an observable tremor. As soon a therapy criterion is observed (e.g., when the oscillation amplitude exceeds a threshold level), a neurostimulator according to the invention causes a responsive electrical signal to be applied to terminate the undesired tremor oscillations. When such an electrical signal is applied, previous studies have shown that involuntary motion can be eliminated or at least reduced in severity, even after stimulation is removed. See, e.g., S. Blond et al., "Control of Tremor and Involuntary Movement Disorders by Chronic Stereotactic Stimulation of the Ventral Intermediate Thalamic Nucleus," Journal of Neurosurgery 1992, 77: 62-68.

The implantable neurostimulator of the invention is capable of storing and transmitting data, thereby allowing the refinement of device settings. Accordingly, data received from an implanted neurostimulator will, over time, help each individual patient. Moreover, the accumulation of data from many treated patients over time will facilitate development of optimal programs for detection and stimulation to treat numerous movement and muscle tone disorders.

In spasticity, one problem is the unwanted contraction of muscles that should relax during movement. Detection of movement of the limb (via EEG, EMG, or accelerometer, for example) and responsive stimulation of the thalamus or internal capsule can be used to reduce contraction of muscles that oppose the desired movement. It is envisioned that the spasticity of one side of the body opposite to brain damage can be reduced by thalamic and internal capsule stimulation. A reduction in spasticity or rigidity will frequently make it possible for a patient to move, but with more voluntary effort than in a person without spasticity or rigidity. Accordingly, stimulation and therapy according to the invention will tend to help those who have some ability to move under the spasticity.

It should be understood that the implanted portion of the system could include bilateral electrical signal detection electrodes and bilateral electrodes for providing responsive stimulation. It should also be understood that the electronic circuitry of the implanted portion of the system (called a "control module") can be programmed by external equipment to adjust many of the control module's functions, including both detection and therapy delivery. For example, the threshold voltage level of the signal detected by the brain electrodes can be adjusted to turn on responsive stimulation only after a pre-programmed amplitude level has been exceeded. Also the parameters of the responsive stimulation signal applied by the deep brain electrodes can be programmed by via external equipment into the electronic circuitry of the control module. For example, the frequency, amplitude and pulse train characteristics of the control module output circuitry is programmable by the means of electrical equipment that is external to the patient. Furthermore, the system can be used to select which electrodes of the array of electrodes are used for signal detection and which are to be used for responsive stimulation. It should be understood that the same electrodes can be used both for signal detection and for responsive or programmed stimulation.

It is envisioned that the control module will also include the capability for multi-channel recording of the electrical input signals that it receives from any of the system's deep brain electrodes, which signal is a form of the patient's electroencephalogram (EEG). Additionally, electromyographic (EMG) voltage signals from muscles that are being controlled by that portion of the brain that is being stimulated, as well as other types of signals (such as from an accelerometer) may also be recorded within the memory of the control module. The control module can be programmed to determine which electrode(s) will be the source of the EEG signal to be recorded. The external equipment can cause the control module to read out either or both real time and/or recorded EEG or EMG signals. Other telemetry data that can be read out includes, but is not limited to, battery voltage, the time when a data recording was made, the setting of the threshold detection voltage and a tabulation of which of the multiple electrodes of the implanted portion of the system are being used for signal detection and which electrodes are being used for stimulation of the brain tissue.

It should be understood that, as compared to continuous stimulation, responsive stimulation has several distinct advantages. A first advantage is decreased use of electrical energy thereby prolonging battery life. A second advantage is reduced habituation, the build-up of tolerance of the brain tissue exposed to the electrical stimulation signal. Reduced tolerance build-up is expected because the stimulation signal is not continuously applied but is applied only when conditions dictate. Finally, and of primary importance in many patients, to the extent continuous stimulation may result in undesired side effects, such as uncomfortable sensory effects and slurring of speech, selectively intermittent programmed and responsive stimulation can reduce those side effects.

An embodiment of the present invention also includes an externally located patient operated initiating device that can be used by the patient to operate the implanted control module. Specifically, the patient operated initiating device can be used to turn on or off the stimulation and/or other functions of the control module if that function is or is not desired. For example, the patient operated initiating device can be used to turn off responsive or continuous stimulation if the patient is about to go to sleep or is merely watching television or doing any other activity where an involuntary motion or muscle tone disorder is not disturbing to the patient. This function has the potential to increase battery longevity even further. The patient operated initiating device could also be used for other functions such as retaining in memory a particular EEG signal portion that the patient believes to be of interest in the treatment of his or her disorder.

As motion disorders rarely occur during sleep, it is envisioned that the implanted device could have an orientation sensor that can determine whether the patient is lying down, sitting, or standing up. Such a detector could allow for reduced power consumption. It is also envisioned that with electrodes deep into the brain, specific sleep EEG patterns can be recorded and a "sleep detector" could be programmed into the detection subsystem within the control module to allow stimulation to be disabled during sleep. REM sleep has specific detectable EEG patterns that are well known. As stated above, an alternative method of reducing power consumption during sleep is to have the internal clock or the patient using a patient control device, turn off the neurostimulator for a specified period during sleep.

It is further envisioned that in addition to providing electrical stimulation, an implantable neurostimulator according to the invention can include an implanted drug pump to responsively (or programmably) release a medication to assist in the control of an involuntary motion or a muscle tone disorder. Still further, it is envisioned that a combination of electrical stimulation and medication release can be used for responsively treating involuntary motion or muscle tone disorders.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
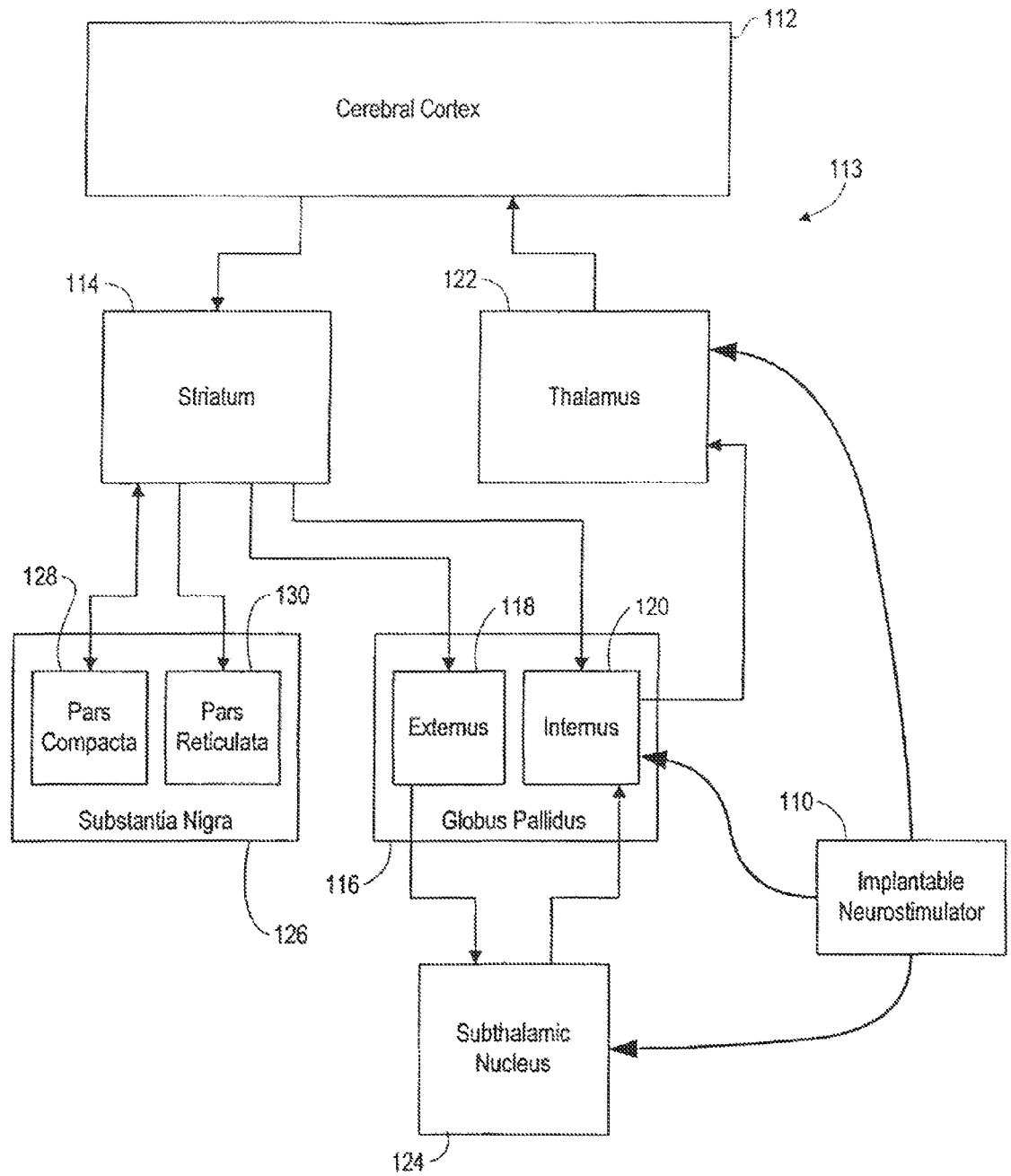
FIG. 1 is a functional block diagram illustrating structures of the human brain believed responsible for voluntary and involuntary movement.

FIG. 1 illustrates several portions of the human brain that are believed to be the primary structures involved in voluntary and involuntary movement. An implantable neurostimulator 110 according to the invention, which will be described in additional detail below, interacts with these structures to control movement disorders.

Movements are initiated and executed via the cerebral cortex 112, in particular the motor cortex. However, movements are controlled and regulated through inhibitory inputs from the basal ganglia 113, a collection of brain structures 114-122 described in general below.

The striatum 114, which includes the caudate and putamen, receives inputs from the cerebral cortex 112. In turn, the striatum communicates with the globus pallidus 116, and in particular provides inputs to the globus pallidus externus (GPe) 118 and the globus pallidus internus (GPi) 120. The GPi 120 then provides its information to the thalamus 122, which tends to regulate and inhibit activity in the cerebral cortex 112 as necessary for controlled movement. Concurrently, the GPe 118 also sends information to the subthalamic nucleus 124, which then controls the activity of the GPi 120 (and hence the thalamus 122). The striatum 114 also communicates with the substantia nigra 126—it sends inputs to the substantia nigra pars compacta (SNc) 128 and the substantia nigra pars reticulata (SNr) 130, and receives feedback from the SNc 128.

In individuals without movement disorders, this complex scheme of inhibitory regulation provided by the thalamus 122 to the cerebral cortex 112 permits finely controlled muscle movements. However, in patients with movement disorders, dysfunction of one or more structures of the basal ganglia contributes to the symptoms of uncontrolled or poorly controlled movements. Accordingly, because these structures of the basal ganglia generally collectively provide an inhibitory effect to the cerebral cortex, several of the movement disorders described herein are generally characterized by tremor, chorea, and other forms of undesired and involuntary movement.

It has been found (by Cooper et al., referenced above, among others) that electrical stimulation of various basal ganglia structures can result in relief from certain symptoms of movement disorders. However traditional attempts at electrical stimulation have encountered side effects and have the disadvantages noted above. Accordingly, a system according to the invention is enabled to provide responsive treatment, only when necessary, by providing the implantable neurostimulator 110 with detection capabilities and stimulation capabilities. As with traditional non-responsive devices, stimulation may be advantageously applied to the GPi 120, the thalamus 122, the subthalamic nucleus 124, or any other structure of the basal ganglia (or elsewhere in the brain) that provides relief.

It should be noted that the functional relationships among various brain structures are generally not very well understood, and that the foregoing description is intended for purposes of illustration of the invention and not as a definitive guide to brain activity involved in movement.

Figure 2:
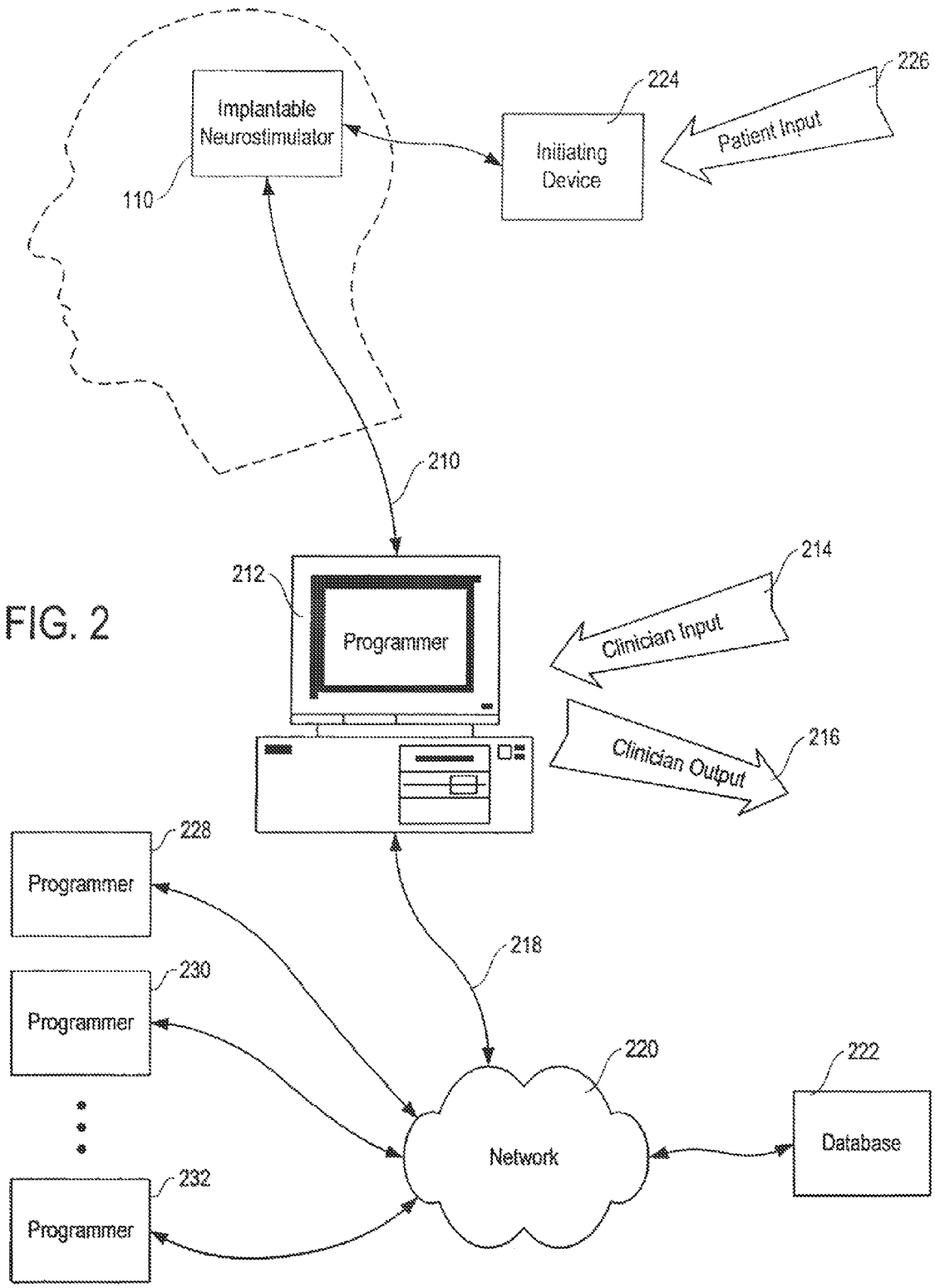
FIG. 2 is a block diagram of an implantable neurostimulator system according to the invention used in conjunction with external equipment.

As stated above, and as illustrated in FIG. 2, a neurostimulator according to the invention operates in conjunction with external equipment. The implantable neurostimulator 110 is mostly autonomous (particularly when performing its usual sensing, detection, and stimulation capabilities), but preferably includes a selectable part-time wireless link 210 to external equipment such as a programmer 212. In the disclosed embodiment of the invention, the wireless link 210 is established by moving a wand (or other apparatus) having communication capabilities and coupled to the programmer 212 into communication range of the implantable neurostimulator 110. The programmer 212 can then be used to manually control the operation of the device, as well as to transmit information to or receive information from the implantable neurostimulator 110. Several specific capabilities and operations performed by the programmer 212 in conjunction with the device will be described in further detail below.

The programmer 212 is capable of performing a number of advantageous operations in connection with the invention. In particular, the programmer 212 is able to specify and set variable parameters in the implantable neurostimulator 110 to adapt the function of the device to meet the patient's needs, upload or receive data (including but not limited to stored EEG waveforms, parameters, or logs of actions taken) from the implantable neurostimulator 110 to the programmer 212, download or transmit program code and other information from the programmer 212 to the implantable neurostimulator 110, or command the implantable neurostimulator 110 to perform specific actions or change modes as desired by a physician operating the programmer 212. To facilitate these functions, the programmer 212 is adapted to receive clinician input 214 and provide clinician output 216; data is transmitted between the programmer 212 and the implantable neurostimulator 110 over the wireless link 210.

The programmer 212 may be used at a location remote from the implantable neurostimulator 110 if the wireless link 210 is enabled to transmit data over long distances. For example, the wireless link 210 may be established by a short-distance first link between the implantable neurostimulator 110 and a transceiver, with the transceiver enabled to relay communications over long distances to a remote programmer 212, either wirelessly (for example, over a wireless computer network) or via a wired communications link (such as a telephonic circuit or a computer network).

The programmer 212 may also be coupled via a communication link 218 to a network 220 such as the Internet. This allows any information uploaded from the implantable neurostimulator 110, as well as any program code or other information to be downloaded to the implantable neurostimulator 110, to be stored in a database 222 at one or more data repository locations (which may include various servers and network-connected programmers like the programmer 212). This would allow a patient (and the patient's physician) to have access to important data, including past treatment information and software updates, essentially anywhere in the world that there is a programmer (like the programmer 212) and a network connection. Alternatively, the programmer 212 may be connected to the database 222 over a trans-telephonic link.

In yet another alternative embodiment of the invention, the wireless link 210 from the implantable neurostimulator 110 may enable a transfer of data from the neurostimulator 110 to the database 222 without any involvement by the programmer 212. In this embodiment, as with others, the wireless link 210 may be established by a short-distance first link between the implantable neurostimulator 110 and a transceiver, with the transceiver enabled to relay communications over long distances to the database 222, either wirelessly (for example, over a wireless computer network) or via a wired communications link (such as trans-telephonically over a telephonic circuit, or over a computer network).

In the disclosed embodiment, the implantable neurostimulator 110 is also adapted to receive communications from an initiating device 224, typically controlled by the patient or a caregiver. Accordingly, patient input 226 from the initiating device 224 is transmitted over a wireless link to the implantable neurostimulator 110; such patient input 226 may be used to cause the implantable neurostimulator 110 to switch modes (on to off and vice versa, for example) or perform an action (e.g., store a record of EEG data). Preferably, the initiating device 224 is able to communicate with the implantable neurostimulator 110 through the communication subsystem 434 (FIG. 4), and possibly in the same manner the programmer 212 does. The link may be unidirectional (as with the magnet and GMR sensor described above), allowing commands to be passed in a single direction from the initiating device 224 to the implantable neurostimulator 110, but in an alternative embodiment of the invention is bi-directional, allowing status and data to be passed back to the initiating device 224. Accordingly, the initiating device 224 may be a programmable PDA or other hand-held computing device, such as the devices manufactured by Palm, Inc. under the marks "PALM PILOT" and "POCKETPC." However, a simple form of initiating device 224 may take the form of a permanent magnet, if the communication subsystem 434 is adapted to identify magnetic fields and interruptions therein as communication signals.

The implantable neurostimulator 110 generally interacts with the programmer 212 as described below. Data stored in the memory subsystem 431 can be retrieved by the patient's physician through the wireless link 210, which operates through the communication subsystem 434 of the implantable neurostimulator 110. In connection with the invention, a software operating program run by the programmer 212 allows the physician to read out a history of events detected including EEG information before, during, and after each event, as well as specific information relating to the detection of each event (such as, in one embodiment, the time-evolving energy spectrum of the patient's EEG). The programmer 212 also allows the physician to specify or alter any programmable parameters of the implantable neurostimulator 110. The software operating program also includes tools for the analysis and processing of recorded EEG records to assist the physician in developing optimized tremor detection parameters for each specific patient.

In an embodiment of the invention, the programmer 212 is primarily a commercially available PC, laptop computer, or workstation having a CPU, keyboard, mouse and display, and running a standard operating system such as WINDOWS by Microsoft Corporation, Linux, UNIX by The Open Company Limited Corporation, or MAC OS by Apple Computer, Inc. It is also envisioned that a dedicated programmer apparatus with a custom software package (which may not use a standard operating system) could be developed.

When running the computer workstation software operating program, the programmer 212 can process, store, play back and display on the display the patient's EEG signals, as previously stored by the implantable neurostimulator 110 of the implantable neurostimulator device.

The computer workstation software operating program also has the capability to simulate the detection and prediction of sensor signal activity representative of movement disorders, such as the tremor described herein. Included in that capability, the software operating program of the present invention has the capability to allow a clinician to create or modify a patient-specific collection of information comprising, in one embodiment, algorithms and algorithm parameters for the detection of relevant sensor signal activity. The patient-specific collection of detection algorithms and parameters used for neurological activity detection according to the invention will be referred to herein as a detection template or patient-specific template. The patient-specific template, in conjunction with other information and parameters generally transferred from the programmer to the implanted device (such as stimulation parameters, time schedules, and other patient-specific information), make up a set of operational parameters for the neurostimulator.

Following the development of a patient specific template on the workstation 212, the patient-specific template would be downloaded through the wireless link 210 from the programmer 212 to the implantable neurostimulator 110.

The patient-specific template is used by the detection subsystem 423 and the CPU 432 of the implantable neurostimulator 110 to detect activity representative of a symptom of a movement disorder in the patient's EEG signals (or other sensor signals), which can be programmed by a clinician to result in responsive stimulation of the patient's brain, as well as the storage of EEG records before and after the detection, facilitating later clinician review.

Preferably, the database 222 is adapted to communicate over the network 220 with multiple programmers, including the programmer 212 and additional programmers 228, 230, and 232. It is contemplated that programmers will be located at various medical facilities and physicians' offices at widely distributed locations. Accordingly, if more than one programmer has been used to upload EEG records from a patient's implantable neurostimulator 110, the EEG records will be aggregated via the database 222 and available thereafter to any of the programmers connected to the network 220, including the programmer 212.

Figure 3:
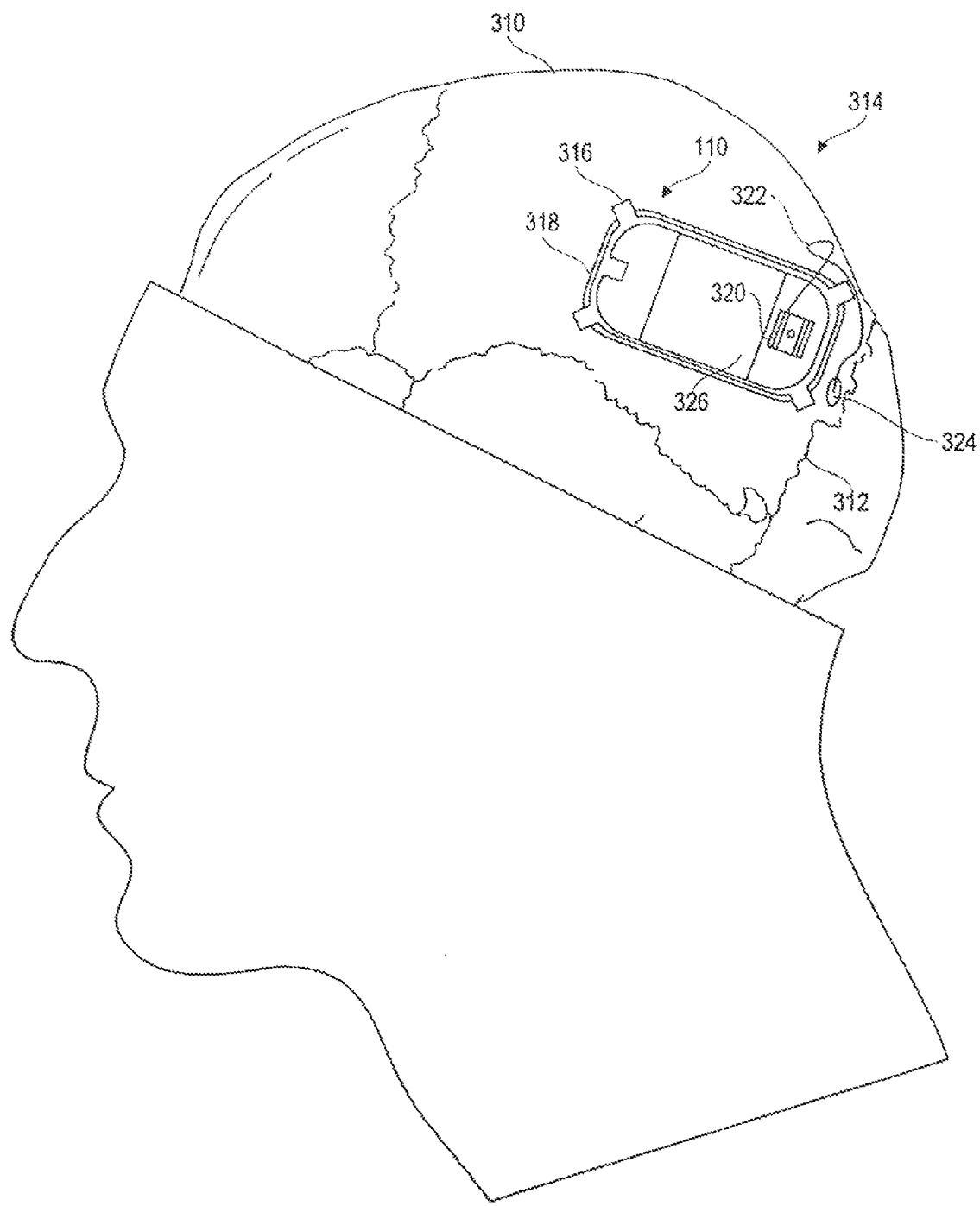
FIG. 3 is a schematic illustration of a patient's cranium showing the implantable neurostimulator of FIG. 2 as implanted, including a lead extending to the patient's brain.

The implantable neurostimulator device 110, as implanted intracranially, is illustrated in greater detail in FIG. 3. The device 110 is affixed in the patient's cranium 314 by way of a ferrule 316. The ferrule 316 is a structural member adapted to fit into a cranial opening, attach to the cranium 314, and retain the device 110.

To implant the device 110, a craniotomy is performed in the parietal bone anterior to the lambdoidal suture 312 to define an opening 318 slightly larger than the device 110. The ferrule 316 is inserted into the opening 318 and affixed to the cranium 314, ensuring a tight and secure fit. The device 110 is then inserted into and affixed to the ferrule 316.

As shown in FIG. 3, the device 110 includes a lead connector 320 adapted to receive one or more electrical leads, such as a first lead 322. The lead connector 320 acts to physically secure the lead 322 to the device 110, and facilitates electrical connection between a conductor in the lead 322 coupling an electrode to circuitry within the device 110. The lead connector 320 accomplishes this in a substantially fluid-tight environment with biocompatible materials.

The lead 322, as illustrated, like other leads for use in a system or method according to the invention, is a flexible elongated member having one or more conductors. As shown, the lead 322 is coupled to the device 110 via the lead connector 320, and is generally situated on the outer surface of the cranium 314 (and under the patient's scalp), extending between the device 110 and a burr hole 324 or other cranial opening, where the lead 322 enters the cranium 314 and is coupled to a depth electrode implanted in a desired location in the patient's brain (such as the GPi 120, the thalamus 122, or the subthalamic nucleus 124). If the length of the lead 322 is substantially greater than the distance between the device 110 and the burr hole 324, any excess may be urged into a coil configuration under the scalp. As described in U.S. Pat. No. 6,006,124 to Fischell, et al. for Means and Methods for the Placement of Brain Electrodes, which is hereby incorporated by reference as though set forth in full herein, the burr hole 324 is sealed after implantation to prevent further movement of the lead 322; in an embodiment of the invention, a burr hole cover apparatus is affixed to the cranium 314 at least partially within the burr hole 324 to provide this functionality.

The device 110 includes a durable outer housing 326 fabricated from a biocompatible material. Titanium, which is light, extremely strong, and biocompatible, is used in analogous devices, such as cardiac pacemakers, and would serve advantageously in this context. As the device 110 is self-contained, the housing 326 encloses a battery and any electronic circuitry necessary or desirable to provide the functionality described herein, as well as any other features. As will be described in further detail below, a telemetry coil may be provided outside of the housing 326 (and potentially integrated with the lead connector 320) to facilitate communication between the device 110 and the external devices described above with reference to FIG. 2.

The neurostimulator configuration described herein and illustrated in FIG. 3 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 316 used for implantation allows the craniotomy to be performed and fit verified without the possibility of breaking the device 110, and also provides protection against the device 110 being pushed into the brain under external pressure or impact. A further advantage is that the ferrule 316 receives any cranial bone growth, so at explant, the device 110 can be replaced without removing any bone screws—only the fasteners retaining the device 110 in the ferrule 316 need be manipulated.

Figure 4:
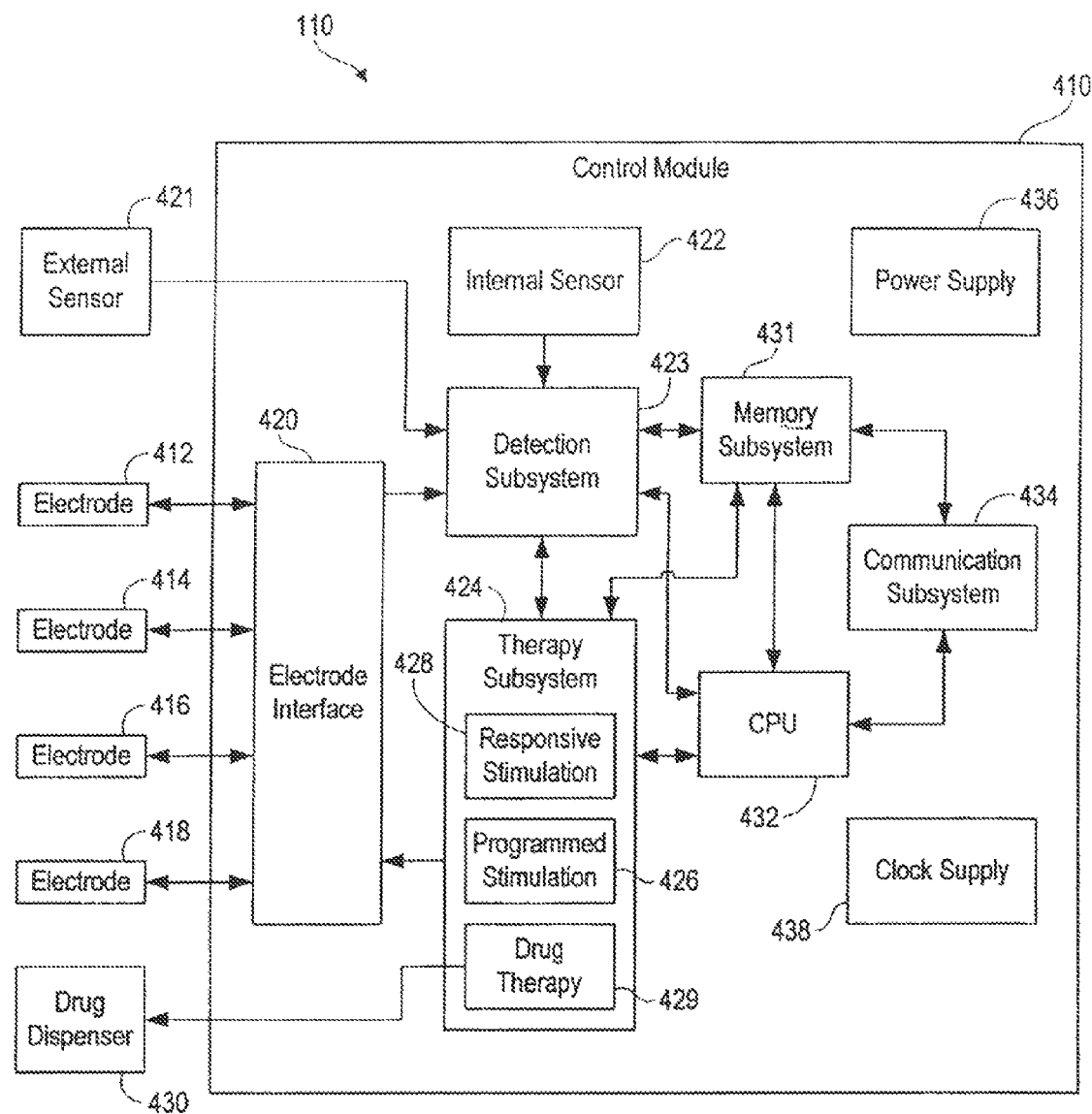
FIG. 4 is a block diagram of the implantable neurostimulator of FIG. 2 for responsive treatment of movement disorders according to the invention.

An overall block diagram of the device 110 used for measurement, detection, and treatment according to the invention is illustrated in FIG. 4. Inside the housing 326 (FIG. 3) of the device 110 are several subsystems making up a control module 410. The control module 410 is capable of being coupled to a plurality of electrodes 412, 414, 416, and 418 (each of which may be connected to the control module 410 via a lead for sensing, stimulation, or both. In the illustrated embodiment, the coupling is accomplished through the lead connector 320 (FIG. 3). Although four electrodes are shown in FIG. 4, it should be recognized that any number is possible, and in the embodiment described in detail below, eight electrodes are used. In fact, it is possible to employ an embodiment of the invention that uses a single lead with at least two electrodes, or two leads each with a single electrode (or with a second electrode provided by a conductive exterior portion of the housing 326 in one embodiment), although bipolar sensing between two closely spaced electrodes on a lead is preferred to minimize common mode signals including noise.

The electrodes 412-418 are connected to an electrode interface 420. Preferably, the electrode interface is capable of selecting each electrode as required for sensing and stimulation. The electrode interface 420 also may provide any other features, capabilities, or aspects, including but not limited to amplification, isolation, and charge-balancing functions, that are required for a proper interface with neurological tissue and not provided by any other subsystem of the device 110. The electrode interface 420, an external sensor 421, and an internal sensor 422 are all coupled to a detection subsystem 423; the electrode interface 420 is also connected to a therapy subsystem 424.

The detection subsystem 423 includes an EEG analyzer function. The EEG analyzer function is adapted to receive EEG signals from the electrodes 412-418, through the electrode interface 420, and to process those EEG signals to identify neurological activity indicative of tremor, involuntary movement, or any other symptom of a movement disorder; various inventive methods for performing such detection are described in detail below.

The detection subsystem may optionally also contain further sensing and detection capabilities, including but not limited to parameters derived from other physiological conditions (such as electrophysiological parameters, temperature, blood pressure, etc.), which may be sensed by the external sensor 421 or the internal sensor 422. These conditions will be discussed in additional detail below. In particular, it may be advantageous to provide an accelerometer or an EMG sensing electrode as the external sensor at a location remote from the implantable neurostimulator 110 (e.g., in one of the patient's limbs that is subject to tremor). The external sensor 421 can be connected to the neurostimulator 110 (and the detection subsystem 423) by a lead or by wireless communication, such as a wireless intrabody signaling technique. To detect head tremor or orientation (e.g., for sleep detection), an accelerometer might be used as the internal sensor 422. Other sensors, such as for temperature, blood pressure, or drug concentration might be implemented as part of the external sensor 421 or the internal sensor 422. Other sensor configurations are of course possible and are deemed within the scope of the invention.

The therapy subsystem 424 is primarily capable of applying electrical stimulation to neurological tissue through the electrodes 412-418. This can be accomplished in any of a number of different manners. For example, it may be advantageous in some circumstances to provide stimulation in the form of a substantially continuous stream of pulses, or on a scheduled basis. This form of stimulation, referred to herein as programmed stimulation, is provided by a programmed stimulation function 426 of the therapy subsystem 424. Preferably, therapeutic stimulation is also provided in response to abnormal events detected by the data analysis functions of the detection subsystem 422. This form of stimulation, namely responsive stimulation, is provided by a responsive stimulation function 428 of the therapy subsystem 424.

As illustrated in FIG. 4, the therapy subsystem 424 and the data analysis functions of the detection subsystem 423 are in communication; this facilitates the ability of therapy subsystem 424 to provide responsive stimulation as well as an ability of the detection subsystem 42 to blank the amplifiers while stimulation is being performed to minimize stimulation artifacts. It is contemplated that the parameters of the stimulation signal (e.g., frequency, duration, waveform) provided by the therapy subsystem 424 would be specified by other subsystems in the control module 410, as will be described in further detail below.

In an embodiment of the invention, the therapy subsystem 424 is also capable of a drug therapy function 429, in which a drug is dispensed from a drug dispenser 430. As with electrical stimulation, this capability can be provided either on a programmed basis (or continuously) or responsively, after an event of some kind is detected by the detection subsystem 423.

Also in the control module 410 is a memory subsystem 431 and a central processing unit (CPU) 432, which can take the form of a microcontroller. The memory subsystem is coupled to the detection subsystem 423 (e.g., for receiving and storing data representative of sensed EEG signals and other sensor data), the therapy subsystem 424 (e.g., for providing stimulation waveform parameters to the stimulation subsystem), and the CPU 432, which can control the operation of the memory subsystem 431. In addition to the memory subsystem 431, the CPU 432 is also connected to the detection subsystem 423 and the therapy subsystem 424 for direct control of those subsystems.

Also provided in the control module 410, and coupled to the memory subsystem 431 and the CPU 432, is a communication subsystem 434. The communication subsystem 434 enables communication between the implantable neurostimulator device 110 (FIG. 1) and the outside world, particularly the external programmer 212 (FIG. 2). As set forth above, the disclosed embodiment of the communication subsystem 434 includes a telemetry coil (which may be situated outside of the housing 326) enabling transmission and reception of signals, to or from an external apparatus, via inductive coupling. Alternative embodiments of the communication subsystem 434 could use an antenna for an RF link or an audio transducer for an audio link.

Rounding out the subsystems in the control module 410 are a power supply 436 and a clock supply 438. The power supply 436 supplies the voltages and currents necessary for each of the other subsystems. The clock supply 438 supplies substantially all of the other subsystems with any clock and timing signals necessary for their operation.

It should be observed that while the memory subsystem 431 is illustrated in FIG. 4 as a separate functional subsystem, the other subsystems may also require various amounts of memory to perform the functions described above and others. Furthermore, while the control module 410 is preferably a single physical unit contained within a single physical enclosure, namely the housing 326 (FIG. 3), it may comprise a plurality of spatially separate units each performing a subset of the capabilities described above. Also, it should be noted that the various functions and capabilities of the subsystems described above may be performed by electronic hardware, computer software (or firmware), or a combination thereof. The division of work between the CPU 432 and the other functional subsystems may also vary—the functional distinctions illustrated in FIG. 4 may not reflect the integration of functions in a real-world system or method according to the invention.

Figure 5:
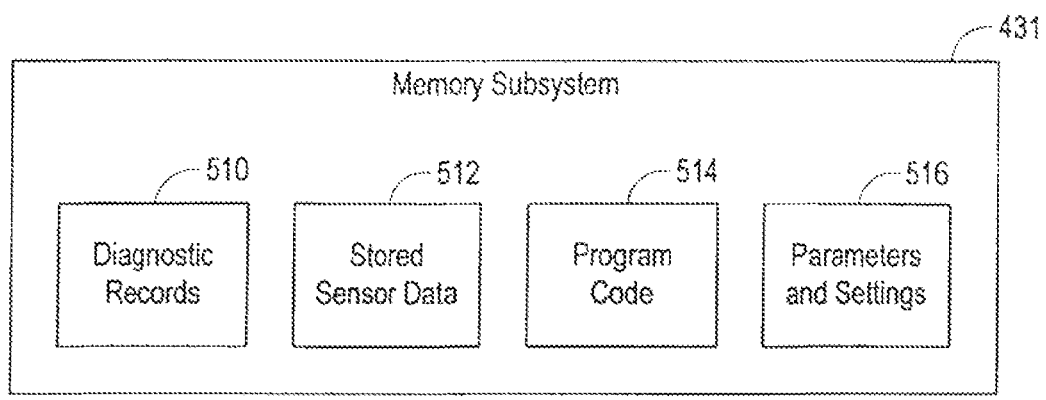
FIG. 5 is a block diagram illustrating data structures stored in a memory subsystem of an implantable neurostimulator according to the invention.

FIG. 5 illustrates the contents of the memory subsystem 431 and the data structures it contains in a system according to the invention.

In particular, as described generally above and in detail below, the implantable neurostimulator 110 is capable of detecting neurological events and conditions characteristic of movement disorders, and is capable of storing such information and communicating it to external equipment such as the programmer 212.

A first storage facility 510 within the memory subsystem 431 is adapted to store diagnostic records received from the implantable neurostimulator 110. In particular, the diagnostic records will generally include the time of and details regarding any neurological events detected by the implantable neurostimulator 110 (such as instances of detected tremor) or actions performed by the implantable neurostimulator 110. For tremor, the details stored among the diagnostic records 510 might include time of day, detected frequency (which, as described above, generally does not vary much between instances in a single patient), amplitude, and what therapeutic actions might have been taken. Possible actions performed might include electrical stimulation applied, mode changes, interrogation attempts, programming attempts, and other operations. For applied electrical stimulation, the specific details recorded among the diagnostic records might include time of day, stimulation waveform used, amplitude, and outcome (i.e., whether the tremor ceased).

A second storage facility 512 within the memory subsystem 431 is adapted to store sensor data. The implantable neurostimulator 110 is capable of recording EEG data from the electrodes 412-418 and other sensor data from external sensors such as external sensor 421 and internal sensors such as internal sensor 422 when conditions dictate (e.g., immediately before and after a detected event, on a scheduled basis, or upon command). For additional information on EEG recording in the context of a neurostimulator used to treat epileptic seizures, see U.S. Pat. No. 6,128,538 for "Means and Methods for the Treatment of Neurological Disorders," filed on Nov. 29, 1999, and issued on Oct. 3, 2000. As would be apparent to a practitioner of ordinary skill, similar considerations apply to a system according to the present invention.

A third storage facility 514 within the memory subsystem 431 stores any program code required for the CPU 432 and any other subsystems of the implantable neurostimulator 110 to operate. In a preferred embodiment of the invention, the program code is updateable via data communications through the communication subsystem 434, thereby enabling the implantable neurostimulator to be reprogrammed or modified as necessary for optimum patient treatment.

Finally, a fourth storage facility 516 within the memory subsystem 431 includes any patient-specific and device-specific settings used in the operation of the implantable neurostimulator 110. The programmer 212 generates these settings based on patient-specific considerations, including the nature of the movement disorder being treated, the locations of the electrodes and the types of sensors being used, and any other relevant factors. Preferably, the programmer 212 is programmed to generate these settings based on an analysis of the patient's EEG and other sensor data, which might have been acquired by and received from the implantable neurostimulator 110 or by other means. Examples of patient-specific parameters would include detection settings (e.g., the amplitude threshold used to identify tremor, as described below) and stimulation settings (e.g., the frequency of electrical stimulation applied to terminate tremor). Many other parameters and settings are of course possible and will not be described in detail here, as they would be apparent to an individual of ordinary skill.

The memory subsystem 431 might also include various other types of data. It should be observed that the various data types described above are intended as illustrative and not comprehensive.

Figure 6:
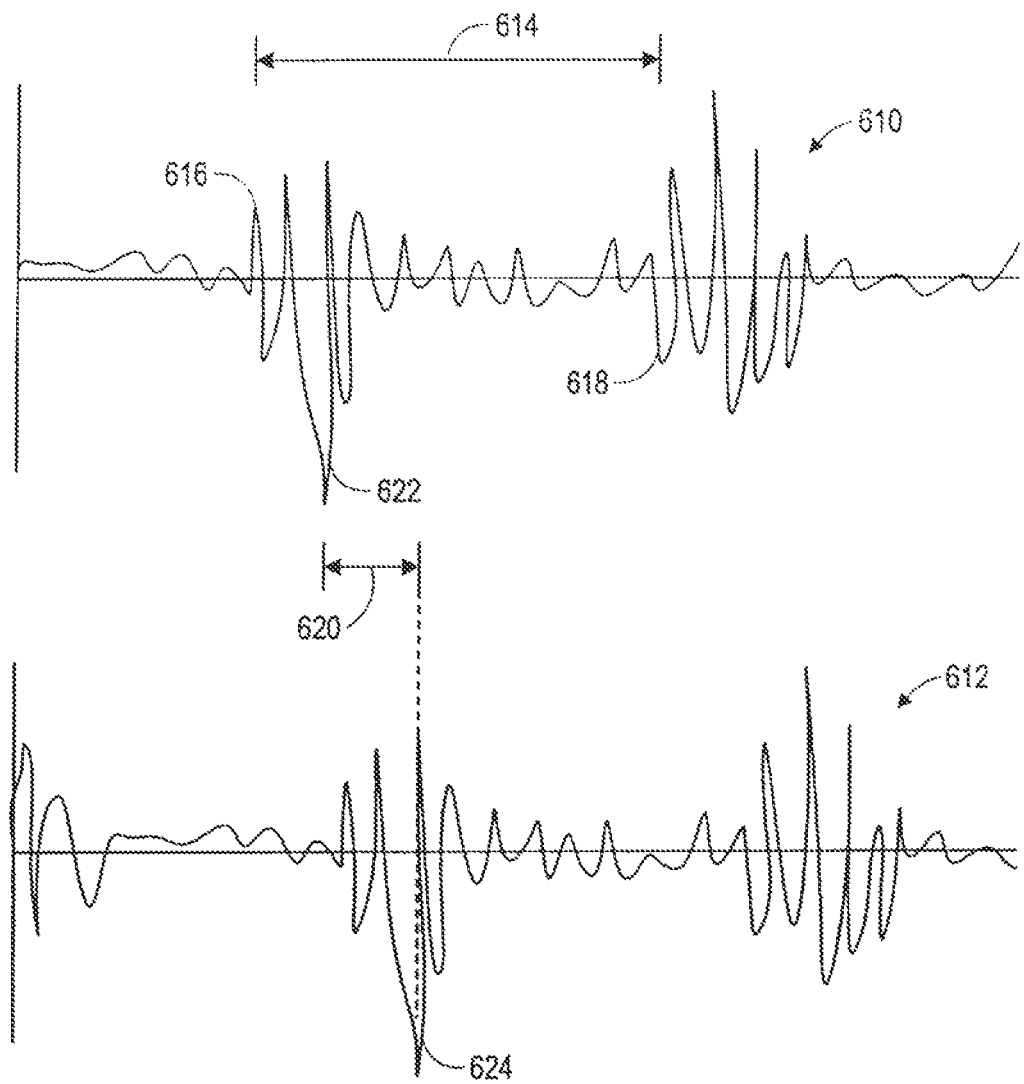
FIG. 6 includes two waveforms depicting tremor observed in a patient's brain and in the same patient's limb, illustrating frequency and phase relationships between the two waveforms.

FIG. 6 depicts two waveforms. It will be observed that when tremor is present, an EEG signal waveform 610 representative of brain activity shares generally the same characteristics (frequency, general morphology) with an EMG signal waveform 612 representative of neuromuscular activity. In particular, a first interval 614 represents the interval between a first tremor burst 616 and a second tremor burst; that first interval 614 in general defines the wave duration (and hence frequency) of the patient's tremor. This duration will vary from patient to patient, but is usually stereotypical of tremor experienced by a single patient.

A second interval 620 represents the interval between a first landmark 622 in the EEG signal 610 and a corresponding second landmark 624 in the same patient's EMG signal 612. This second interval 620 defines the phase difference between the EEG signal 610 and the EMG signal 612. As with the duration and frequency, the phase difference is likely to vary from patient to patient but not within a single patient.

It will be recognized that the fixed frequency and phase difference illustrated in FIG. 6 would tend to make tremor detection possible; a method for accomplishing this is set forth in greater detail with reference to FIG. 9.

The waveforms 610 and 612 are intended for purposes of illustration of frequency and phase relationships only, and do not necessarily represent any actual EEG or EMG signals likely to be found in an actual patient. In particular, the EMG signal waveform 612 is likely to have a substantially different morphology with an increased signal-to-noise ratio in comparison to the EEG signal waveform 610. Other differences may also be present and will be understood by a practitioner of ordinary skill.

In general, a process performed by the implantable neurostimulator 110 for detecting a neurological event or characteristic such as tremor is set forth below, with reference to FIG. 7.

The process begins by receiving a signal (step 710) from one or more brain or peripheral electrodes (such as the electrodes 412-418) or from an internal sensor 422 or an external sensor 421.

The signal is then processed as necessary (step 712) in the analog domain to obtain a usable signal. For example, it may be necessary or desirable to provide signal amplification or filtering to remove unwanted noise, extraneous information in frequency bands not being analyzed, stimulation and amplifier blanking artifacts, and the like.

The signal is digitized (step 714), i.e. the analog signal is converted into a digital data stream. The detection subsystem 423 operates and performs the detection techniques described herein upon digital data, and other subsystems of the implantable neurostimulator 110 also operate in the digital domain. Preferably, digitization is performed at a rate of either 250 or 500 Hz and at a resolution of 8-10 bits.

The digital data is then processed (step 716) and transformed in the digital domain as desired for detection and other purposes. At this stage, after digitization of the signal, generally a digital representation of the analog signal has been obtained, but it may be desirable to transform the data into the frequency domain or obtain other information about the signal through other transformations.

If desired, the digital data is stored (step 718) in the memory subsystem 431, for later retrieval by external equipment. It will be appreciated (and has generally been set forth above) that it may be desirable in some circumstances to store digital data representative of episodes of tremor or other symptoms for later diagnosis by a clinician; this capability may be invoked by programming the implantable neurostimulator 110 to record data at one or more specific times, by programming the neurostimulator 110 to store a specified quantity of pre-trigger and post-trigger sensor data, or by any other desired and clinically advantageous means.

The data is then analyzed (step 720) by the detection subsystem 423 to identify when tremor or other symptoms of the movement disorder are occurring. The methods performed in identifying tremor, in particular, are described in greater detail below with reference to FIGS. 8, 9, 11, and 13.

The data analysis results are checked for the occurrence of an event (step 722), and if one has occurred, an action is performed by the implantable neurostimulator 110. Such actions may include the delivery of treatment (which will be discussed in greater detail below), the storage of sensor data, the storage of a diagnostic record, or any other clinically advantageous function.

Figure 7:
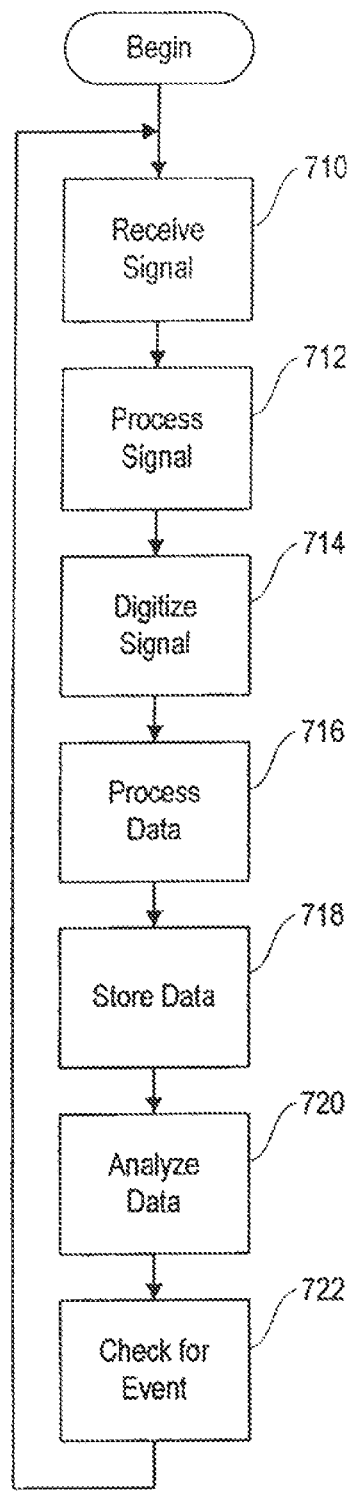
FIG. 7 is a flow chart illustrating a process performed in detecting a neurological event characteristic of a movement disorder in a system according to the invention.

The process illustrated by the flow chart of FIG. 7 is preferably performed in parallel for as many input channels as the implantable neurostimulator 110 has available. As described and illustrated above, one embodiment of the implantable neurostimulator includes eight input channels, any of which may be received from electrodes or other sensors.

Figure 8:
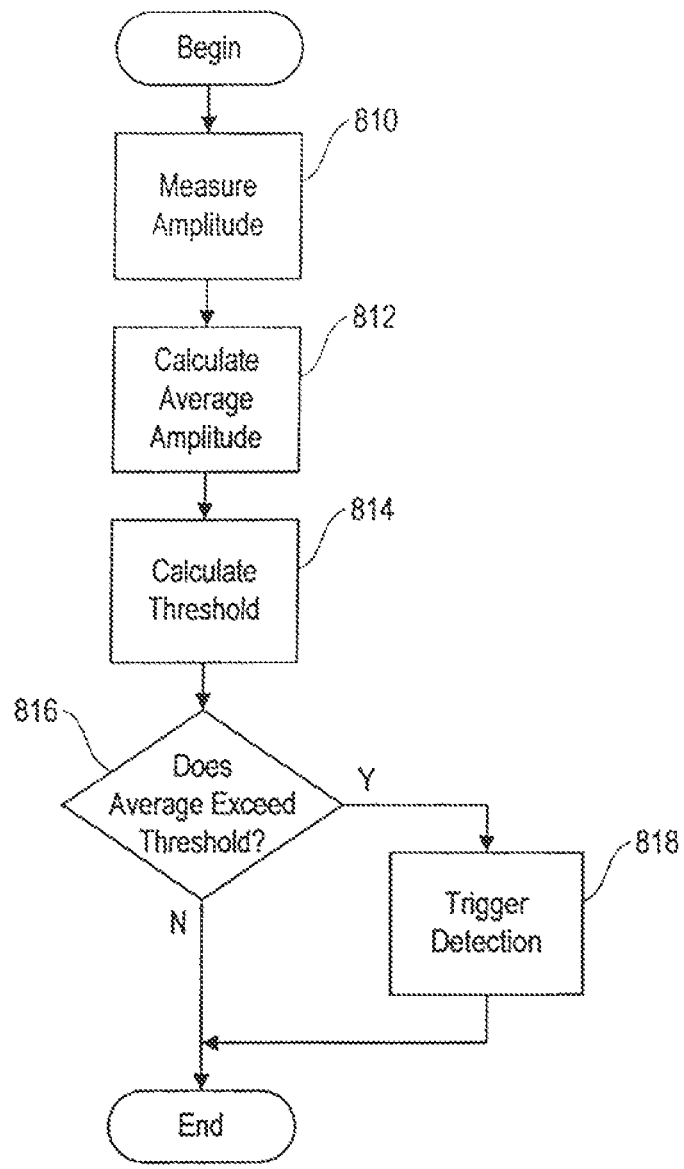
FIG. 8 is a flow chart illustrating a process performed in detecting tremor via thresholded signal amplitude in a system according to the invention.

As referenced above, one method for detecting tremor is illustrated in FIG. 8. The method begins by measuring the amplitude (step 810) of an electrographic signal received from the electrodes 412-418 (or a signal received from some other kind of sensor, such as an accelerometer). The amplitude is generally defined as the difference between the highest positive-going peaks in the signal and the lowest negative-going peaks.

The average amplitude is then calculated over a period of time (step 812). Preferably, the average amplitude is calculated over a period of greater than approximately one second, as this will allow any significant variations present within the 3-5 Hz tremor signals to be averaged out, leaving only the average amplitude of the signals representing tremor.

A threshold is then calculated (step 814) or otherwise obtained. It is expected that the amplitude of any observed electrographic tremor will vary depending on a number of factors, both from patient to patient and even within a single patient. Accordingly, although a single programmed threshold may function to detect tremor, it is believed advantageous to calculate a dynamic threshold value. In an embodiment of the invention, the dynamic threshold is calculated to be a fixed offset or percentage greater than a long-term moving average amplitude of the observed signal that does not include tremor oscillations. This signal can be obtained, for example, from another portion of the patient's brain, or from a tremor-free period (such as shortly after an episode of treatment). If insufficient tremor-free signal data is available, the threshold can be calculated to be slightly lower than the average tremor oscillation amplitude experienced by the patient.

If the average amplitude of the signal exceeds the threshold (step 816), then a detection is triggered (step 818). Generally, as described in greater detail below, the implantable neurostimulator 110 is programmed to perform an action when a detection is triggered—for example to apply therapeutic electrical stimulation or to deliver a dose of a medication.

Regardless of whether a detection has been triggered, an advantageous embodiment of the invention performs the method of FIG. 8 essentially continuously (or when programmed to do so), thereby continuously calculating the average amplitude, updating the threshold, and checking the average amplitude of the signal against the threshold. It will be recognized that this procedure can be performed on multiple input channels, even more than one at the same time.

Figure 9:
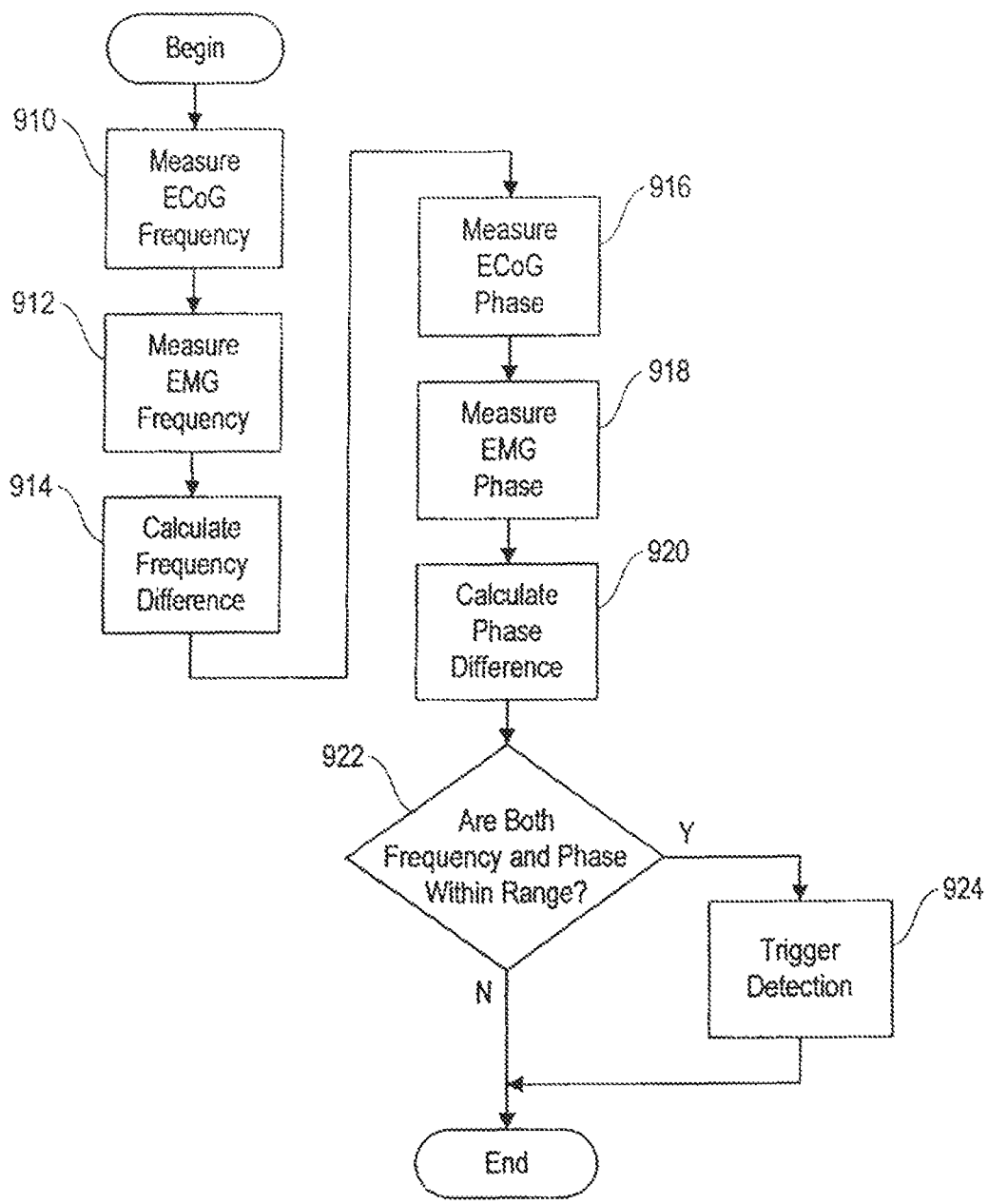
FIG. 9 is a flow chart illustrating a process performed in detecting tremor via the identification of signal frequency and phase relationships in a system according to the invention.

An alternative method for detecting tremor is illustrated in FIG. 9; it detects tremor by relating the frequency and phase of a signal obtained in the patient's brain to the frequency and phase of a signal obtained in a limb that tends to experience tremor. As with the method illustrated by FIG. 8, the method is operative on electrographic data and other types of sensor data, including accelerometer measurements. However, for illustrative purposes, the method is described below with reference to EEG and EMG measurements.

The method begins by measuring a frequency of the patient's EEG (step 910), at a location where tremor is generally observed (such as the thalamus). The frequency of the patient's EMG is also measured (step 912). A signal's frequency can be calculated in several possible ways, including via Fourier (and more easily implemented FFT) transforms, measuring signal amplitude after band pass filtering, and via half waves (which will be illustrated and discussed in greater detail below). The difference between the EEG frequency and the EMG frequency is then calculated (step 914).

The phase of the EEG signal is then observed and measured (step 916). In an embodiment of the invention, phase is represented simply by the time at which a measurable feature of a waveform occurs. For example, in FIG. 6, the first landmark 622 of the patient's EEG signal occurs at a measurable time identified with reference to the clock supply 438. Likewise, the phase of the corresponding EMG signal is observed and measured (step 918). In FIG. 6, the second landmark 624 of the patient's EMG also occurs at a measurable time. The phase difference (in the example of FIG. 6, namely the difference between the time of the first landmark and the time of the second landmark) is calculated (step 920). Preferably, phase measurements and calculations made according to the invention are performed on heavily filtered or otherwise pre-processed signals, so that the measured phase is that of any tremor, not some other feature of the signal (such as ordinary background EEG activity).

When tremor is occurring, it is expected that the patient's EEG and the patient's EMG will both exhibit a measurable component at the same frequency. Accordingly, when tremor is present, the frequency difference will be near zero. Similarly, when tremor is present, the phase of the patient's tremor oscillations in the EEG will bear a fixed relationship to the phase of the patient's tremor oscillations in the EMG. Accordingly, the calculated phase difference will tend to remain near a patient-specific constant (which, in a preferred embodiment of the invention, can be measured and programmed into the implantable neurostimulator 110). If both the frequency difference and the phase difference are within range of their expected values (step 922), then a detection is triggered (step 924), and the device will generally perform an action (such as apply a treatment, switch modes, or store one or more signals for diagnostic purposes).

As with FIG. 8, the method illustrated in FIG. 9 can be performed continuously and on as many channels of data as desired or clinically relevant.

Figure 10:
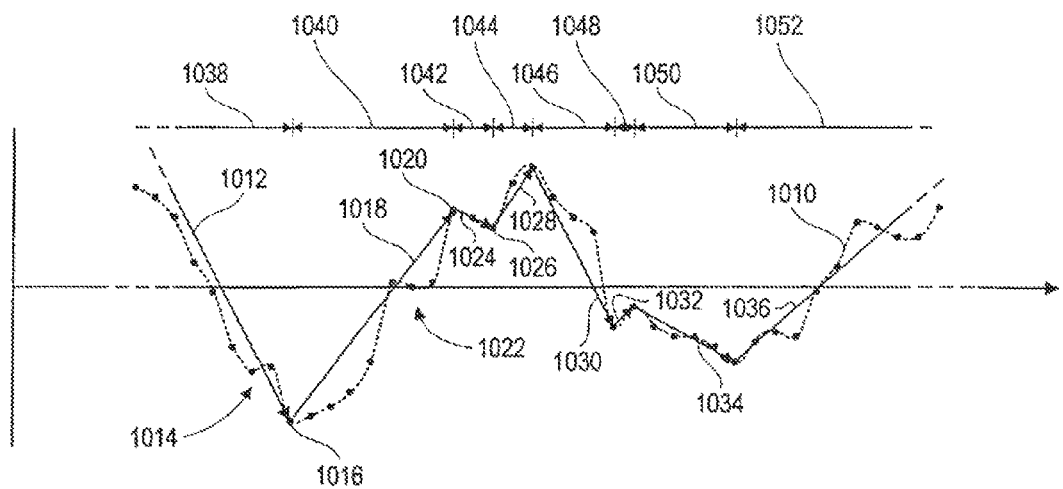
FIG. 10 is a graph of an exemplary intracranial EEG signal, illustrating the extraction of half waves from the signal for neurological event detection purposes.

Referring now to FIG. 10, one advantageous form of processing by the detection subsystem 423, namely qualified half wave measurement, is described in conjunction with a filtered and sampled waveform 1010. The waveform 1010 is considered herein to be generally representative of an EEG signal obtained and initially processed according to the invention. Initially, half waves in general will be described herein as background information for the subsequent description of a detection method employing half waves.

In a first half wave 1012, which is partially illustrated in FIG. 10 (the starting point occurs before the illustrated waveform segment 1010 begins), the waveform segment 1010 is essentially monotonically decreasing, except for a small first perturbation 1014. Accordingly, the first half wave 1012 is represented by a vector from the starting point (not shown) to a first local extremum 1016, where the waveform starts to move in the opposite direction. The first perturbation 1014 is of insufficient amplitude to be considered a local extremum, and is disregarded by a hysteresis mechanism (discussed in further detail below). A second half wave 1018 extends between the first local extremum 1016 and a second local extremum 1020. Again, a second perturbation 1022 is of insufficient amplitude to be considered an extremum. Likewise, a third half wave 1024 extends between the second local extremum 1020 and a third local extremum 1026; this may appear to be a small perturbation, but is greater in amplitude than a selected hysteresis threshold. The remaining half waves 1028, 1030, 1032, 1034, and 1036 are identified analogously. As will be discussed in further detail below, each of the identified half waves 1012, 1018, 1024, 1028, 1030, 1032, 1034, and 1036 has a corresponding duration 1038, 1040, 1042, 1044, 1046, 1048, 1050, and 1052, respectively, and analogously, a corresponding amplitude determined from the relative positions of each half wave's starting point and ending point along the vertical axis, and a slope direction, increasing or decreasing. If a half wave's duration and amplitude both exceed fixed or programmable thresholds, then the observed half wave is large (and hence significant) enough to be considered a qualified half wave.

In a method performed according to the invention, it is particularly advantageous to allow for a programmable hysteresis setting in identifying the ends of half waves. In other words, as explained above, the end of an increasing or decreasing half wave might be prematurely identified as a result of quantization (and other) noise, low-amplitude signal components, and other perturbing factors, unless a small hysteresis allowance is made before a reversal of waveform direction (and a corresponding half wave end) is identified. Hysteresis allows for insignificant variations in signal level inconsistent with the signal's overall movement to be ignored without the need for extensive further signal processing such as filtering. Without hysteresis, such small and insignificant variations might lead to substantial and gross changes in where half waves are identified, leading to unpredictable results.

Figure 11:
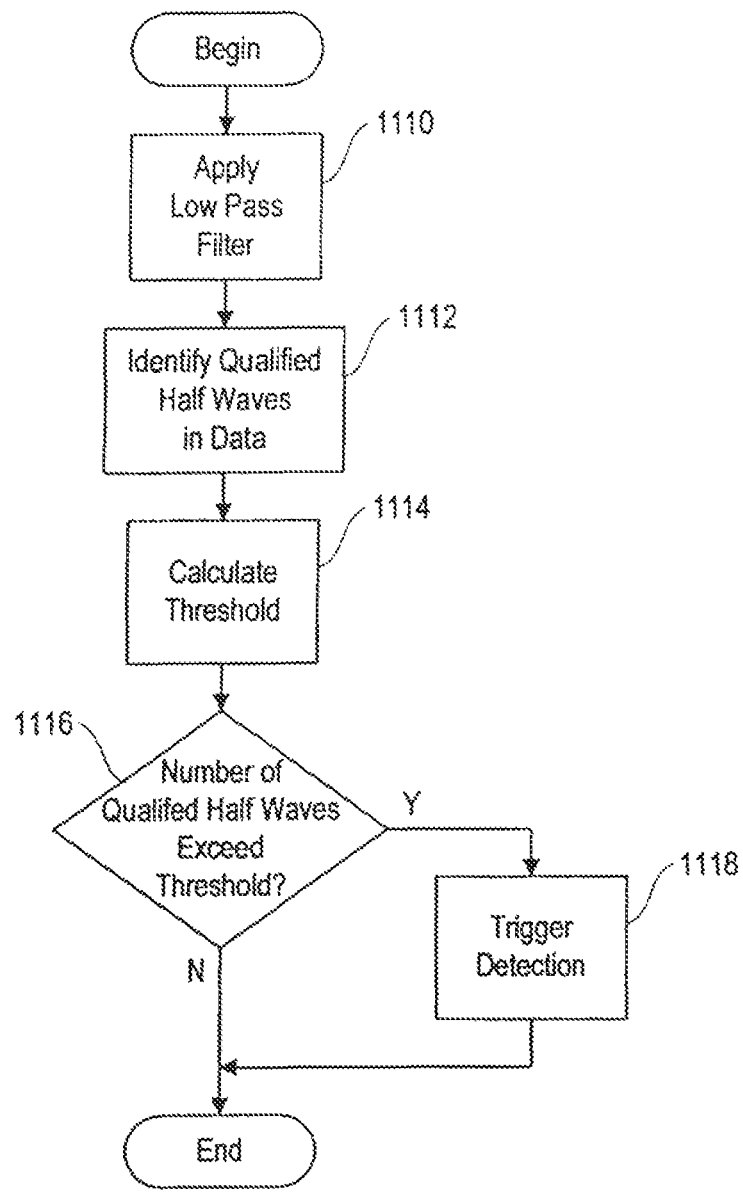
FIG. 11 is a flow chart illustrating a process performed in detecting tremor via the identification of half waves in an EEG signal in a system according to the invention.

As described above, measuring signal half waves is an advantageous technique in determining whether tremor is present in a measured signal, either EEG or from some other sensor. A method for using half waves to identify tremor is illustrated in FIG. 11.

Initially, to isolate a signal suitable for half wave measurement, a low pass filter is applied (step 1110) to a signal (such as an EEG signal) that tends to include information representative of tremor. As described above, an EEG signal (and to a lesser extent, an EMG signal) contains a significant amount of information that is not related to tremor; much of this appears to be background activity; it generally appears in frequency bands outside of the 3-5 Hz band where tremor is usually found. For half wave measurements to perform effectively in a system according to the invention, as much of this noise as possible should be removed. One way to accomplish this is through low-pass filtering. Other methods are of course possible, one of which will be described below with reference to FIG. 13.

The parameters for qualified half wave detection are preferably set to identify those half waves that are components of signals in the 3-5 Hz range. Qualified half waves in the signal are then identified (step 1112).

As described above, qualified half waves are generally counted within a specified time window (which is preferably long enough to capture enough half waves to reduce percentage errors caused by small perturbations in the signal, for example five seconds).

A threshold is then calculated (step 1114) based on historical half wave measurements over a longer time period. Analogously to the amplitude threshold-based tremor detection method illustrated in FIG. 8, the threshold is preferably calculated as a fixed or percentage offset over a long-term trend of half wave measurements (e.g., over minutes) that do not represent tremor (or represent a clinically acceptable level of tremor), but if such a trend is not available, the threshold can be calculated to be slightly below typical observed tremor levels. A combination of the approaches is also possible.

If the number of qualified half waves (that is, the number of half waves of an amplitude and duration sufficient to be considered representative of the signal) exceeds the threshold (step 1116), then a detection is triggered (step 1118) and the device generally is programmed to perform an action.

As with FIGS. 8-9, the method illustrated in FIG. 11 can be performed continuously and on as many channels of data as desired or clinically relevant.

As will be described in greater detail below, the area under the curve of a waveform is another useful calculation that can be employed in the detection of tremor related to a movement disorder. The concept of area under a waveform's curve is described initially, and will provide background information for the subsequent discussion of a detection scheme that employs the calculation.

Figure 12:
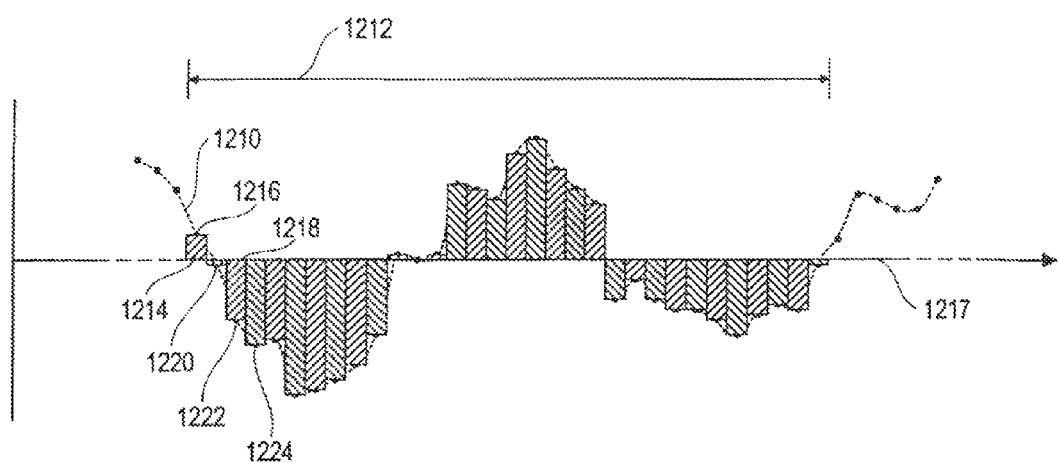
FIG. 12 is a graph of an exemplary intracranial EEG signal, illustrating the calculation of an area function representative of the signal for neurological event detection purposes.

FIG. 12 illustrates the waveform of FIG. 10 with area under the curve identified within an exemplary time window. Area under the curve, which in some circumstances is somewhat representative of a signal's energy (though energy of a waveform is more accurately represented by the area under the square of a waveform), is another signal processing and detection method used in accordance with the invention.

The total area under the curve represented by a waveform 1210 within the window 1212 is equal to the sum of the absolute values of the areas of each rectangular region of unit width vertically bounded by the horizontal axis and the sample. For example, the first contribution to the area under the curve within the window 1212 comes from a first region 1214 between a first sample 1216 and a baseline 1217. A second contribution to the area under the curve within the window 1212 comes from a second region 1218, including areas between a second sample 1220 and the baseline 1217. There are similar regions and contributions for a third sample 1222 and the baseline 1217, a fourth sample 1224 and the baseline 1217, and so on. It should be observed that the region widths are not important—the area under each sample can be considered the product of the sample's amplitude and a unit width, which can be disregarded. In a similar manner, each region is accumulated and added to the total area under the curve within the window 1212. Although the concept of separate rectangular regions is a useful construct for visualizing the idea of area under a curve, it should be noted that a process for calculating area need not partition areas into regions as shown in FIG. 12—it is only necessary to accumulate the absolute value of the waveform's amplitude at each sample, as the unit width of each region can be disregarded.

Figure 13:
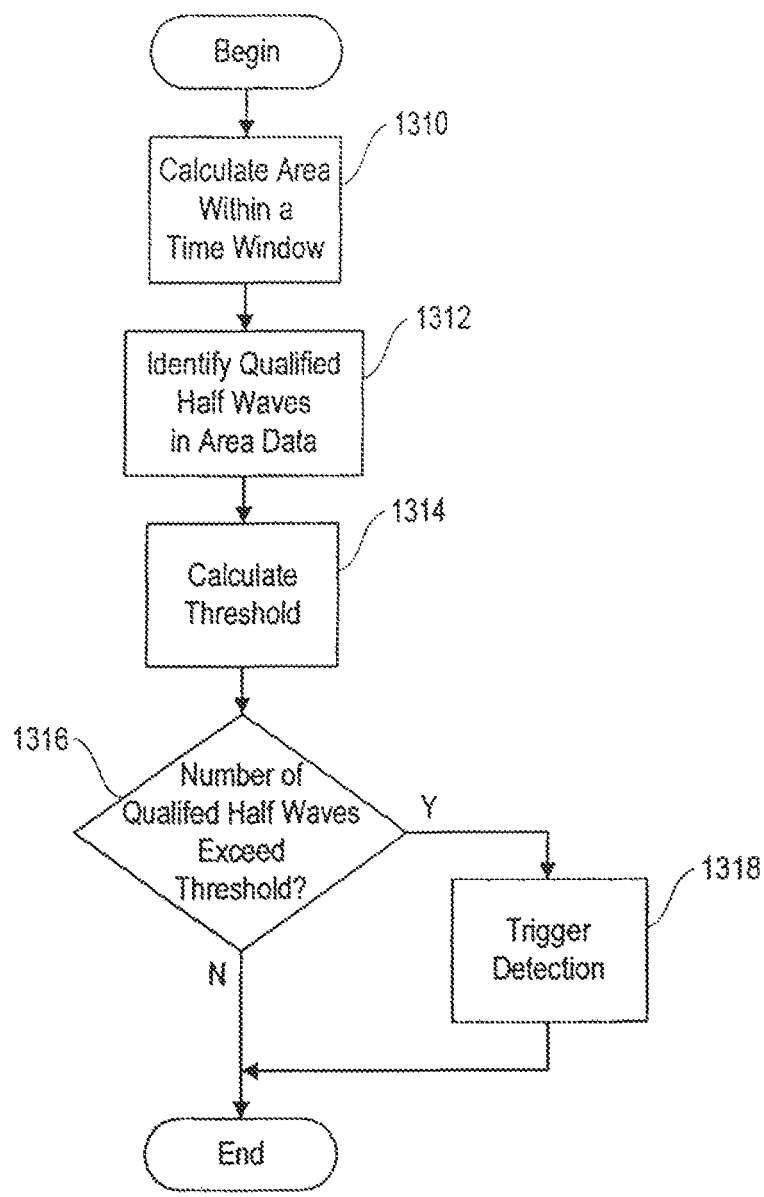
FIG. 13 is a flow chart illustrating a process performed in detecting tremor via the identification of half waves in a signal representative of signal activity in a system according to the invention.

As described above, measuring signal half waves is an advantageous technique in determining whether tremor is present in a measured signal, either EEG or from some other sensor. An alternative method for using half waves to identify tremor is illustrated in FIG. 13. It involves using an advantageous configuration for the detection of tremor, in which a signal area calculation is performed (as described above with reference to FIG. 12), and the resulting string of measurements is fed as a signal into a half wave calculation. This method is illustrated in FIG. 13.

Initially, to isolate a signal suitable for half wave measurement, the area measurement scheme described above can be used to remove sensor signal noise not relevant for tremor identification. Initially, an area (as described above) is calculated over a short time window, which in the described embodiment is on the order of tens of milliseconds in length (step 1310). As set forth above, an EEG signal (and to a lesser extent, an EMG signal) contains a significant amount of information that is not related to tremor; much of this appears to be Gaussian noise; it generally appears in frequency bands outside of the 3-5 Hz band where tremor is usually found. For half wave measurements to perform effectively in a system according to the invention, as much of this noise as possible should be removed, and the signal area calculated over a window tends to accomplish this. In addition to the low-pass filtering method described above and illustrated in FIG. 11, other methods are possible and will be understood by a practitioner of ordinary skill in the art. In particular, it will be recognized that it is also possible to calculate the line length of the sensor signal (see U.S. Pat. No. 8,810,285 to Pless et al. for "Seizure Sensing and Detection Using an Implantable Device," filed on Jun. 28, 2001, issued Oct. 26, 2004, for a description); this also tends to remove extraneous information from the signal, but is believed to be more sensitive to transients and noise than the area under the curve described above.

A sequence of area measurements for consecutive windows is thereby generated, and that sequence of measurements is provided as an input to a half wave measurement function, using a time window substantially longer than that used for the area calculation.

The parameters for qualified half wave detection are preferably set to identify those half waves that are components of signals in the 3-5 Hz range. Qualified half waves in the signal are then identified (step 1312).

As described above, qualified half waves are generally counted within a specified time window (which is preferably long enough to capture enough half waves to reduce percentage errors caused by small perturbations in the signal, for example five seconds).

A threshold is then calculated (step 1314) based on historical half wave measurements over a longer time period. Analogously to the amplitude threshold-based tremor detection method illustrated in FIG. 8, the threshold is preferably calculated as a fixed or percentage offset over a long-term trend of half wave measurements (e.g., over minutes) that do not represent tremor (or represent a clinically acceptable level of tremor), but if such a trend is not available, the threshold can be calculated to be slightly below typical observed tremor levels. A combination of the approaches is also possible.

If the number of qualified half waves (that is, the number of half waves of an amplitude and duration sufficient to be considered representative of the signal) exceeds the threshold (step 1316), then a detection is triggered (step 1318) and the device generally is programmed to perform an action.

As with FIGS. 8, 9 and 11, the method illustrated in FIG. 13 can be performed continuously and on as many channels of data as desired or clinically relevant.

Figure 14:
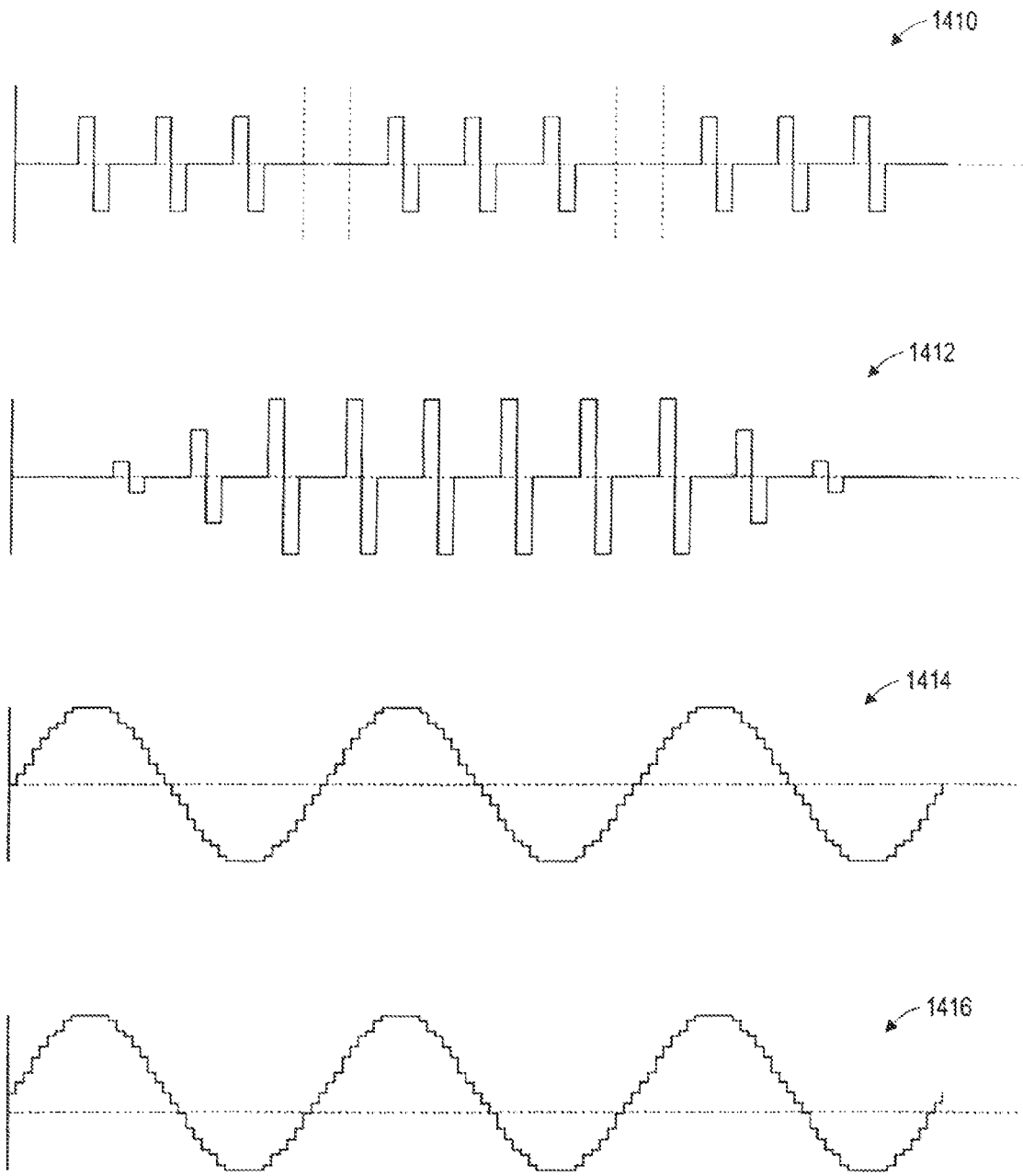
FIG. 14 illustrates several possible stimulation waveforms advantageously employed to control movement disorders with a system according to the invention.

FIG. 14 illustrates several possible waveform morphologies that might be advantageously employed for the treatment of movement disorders with an implantable neurostimulator according to the invention.

A first waveform 1410 comprises a plurality of bursts of biphasic pulses. In an embodiment of the invention, it may be advantageous to apply several consecutive bursts of pulses, as illustrated, to disrupt the neurological activity that results in tremor. A limited number of bursts may be applied at any given time. It should be recognized that the amplitude, duration, and inter-pulse interval for each pulse in a burst can preferably be varied by programming the implantable neurostimulator 110 accordingly. In an embodiment of the invention, each pulse within a burst can be varied individually. Moreover, it is preferably possible also to program different burst lengths and inter-burst intervals, as well as the number of bursts applied in any single treatment.

A second waveform 1412 comprises, as illustrated, a single burst of biphasic pulses. Unlike the bursts illustrated in the first waveform 1410, however, the beginning of the burst "ramps" up to a maximum amplitude, and the end of the burst ramps back down to zero. This morphology is considered to provide some relief to patients who experience unpleasant sensory side effects when stimulation is abruptly begun and ended.

In a manner similar to the first waveform 1410, the second waveform 1412 can also be applied multiple times in succession if it is advantageous to do so. As with the first waveform 1410, numerous parameters can be varied to different effect; durations for the beginning ramp-up and the ending ramp-down are preferably also able to be specified and programmed in a system according to the invention according to a particular patient's clinical needs.

A third waveform 1414 comprises a digitized approximation of a sinusoidal morphology. This third waveform 1414 might be advantageously employed to disrupt or otherwise terminate the symptoms of a movement disorder in certain patients. In particular, the third substantially sinusoidal waveform 1414 is particularly well suited to low frequency use.

A fourth waveform 1416 comprises a waveform similar to that of the third waveform 1414, but with a direct current (DC) component added. Stimulation with small direct currents may be clinically advantageous in certain circumstances, but care must be taken to avoid charge densities that might result in tissue damage.

It should be noted that the waveforms of FIG. 14 are not to scale, and in particular the relationship between pulse duration and inter-pulse interval may be different in a functioning embodiment of the invention from what is illustrated here. The waveforms illustrated in FIG. 14 are for purposes of illustration only, and as would be recognized by a practitioner of ordinary skill in the art, would not necessarily be advantageous in any particular clinical application.

Any of the waveforms of FIG. 14 are suitable for use in either responsive stimulation or programmed stimulation according to the invention, and will result in significant benefits in comparison to continuous stimulation when applied intermittently. One or more of these waveforms 1410-1416 can also be applied in conjunction with drug therapy delivered from the drug dispenser 430 (FIG. 4), either in the same location in the patient's body or in different locations.

Figure 15:
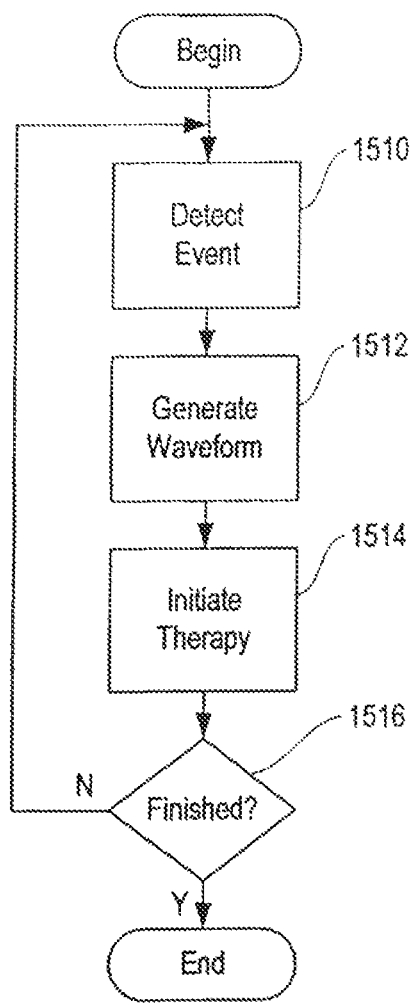
FIG. 15 is a flow chart illustrating a process performed in applying electrical stimulation therapy for a movement disorder with a system according to the invention.

FIG. 15 depicts a flow chart illustrating the method by which a neurostimulation system (such as the implantable neurostimulator device 110, FIG. 1) provides adaptive and synchronized therapy according to an embodiment of the invention. Initially, as described above with reference to FIG. 7, the system receives EEG data or other electrographic or sensor signals—this is generally performed on a continuous basis, alongside and in parallel with any other detection and other operations performed by the neurostimulator device 110. Also preferably concurrently, the EEG data is processed, analyzed, and stored.

Figure 17:
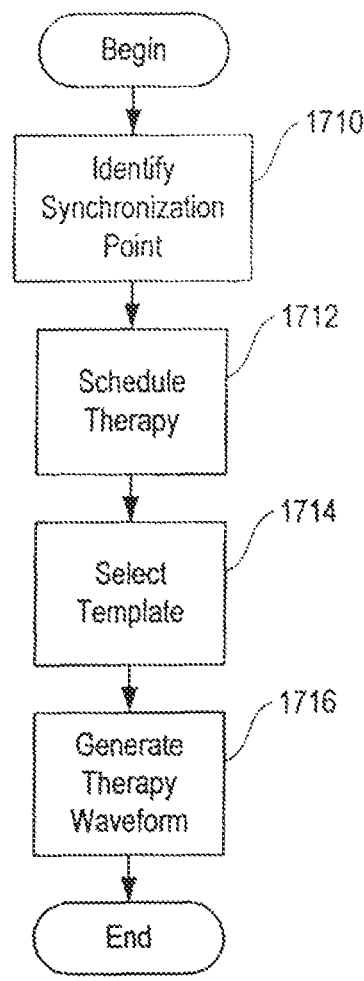
FIG. 17 is a flow chart illustrating a process performed in correlating the application of electrical stimulation therapy to a detected neurological event.

A neurological event is then detected (step 1510), or some other time-related event occurs (such as receipt of a time scheduling interrupt from the CPU 432). Following the event, a treatment waveform, including stimulation time and signal details, is generated (step 1512). The treatment waveform generation process for synchronized stimulation is illustrated in FIG. 17 and described below, and generally involves extracting information from a measured electrographic signal via the detection subsystem 423 and generating a waveform representative of an adaptive stimulation signal based on the extracted information. Otherwise, any desired waveform (such as those illustrated in FIG. 14) can be employed, and need not be created in real time.

Application of the generated stimulation therapy is then initiated (step 1514) at the appropriate time. The process used to initiate therapy is described below. Preferably, stimulation is applied in parallel with other operations performed by the implantable neurostimulator device 110, so even while stimulation is ongoing, if the neurostimulator device 110 is not finished applying adaptive stimulation therapy (step 1516), the process of FIG. 15 can repeat as necessary.

Therapy is initiated and applied at a clinically appropriate time according to the methods described below. Delivery of stimulation is scheduled by the CPU 432 (FIG. 4) and tied to a timer interrupt. When the timer interrupt is received, synchronization to the therapy schedule has been accomplished, and the CPU 432 commands the therapy subsystem 424 (and in particular the appropriate responsive stimulation 428 or drug therapy 429) to deliver the appropriate therapy, thereby applying stimulation therapy to the patient. The nature of the desired stimulation waveform, if it is simple, can be expressed in the command from the CPU 432, or alternatively, a representation of the desired stimulation waveform, if stored in the memory subsystem 431, can be caused by the CPU 432 to be streamed to the stimulation subsystem 424. If there are additional scheduled pulses or waveforms to be applied, the therapy plan is optionally revised, and the synchronization and application steps are repeated as necessary.

Figure 16:
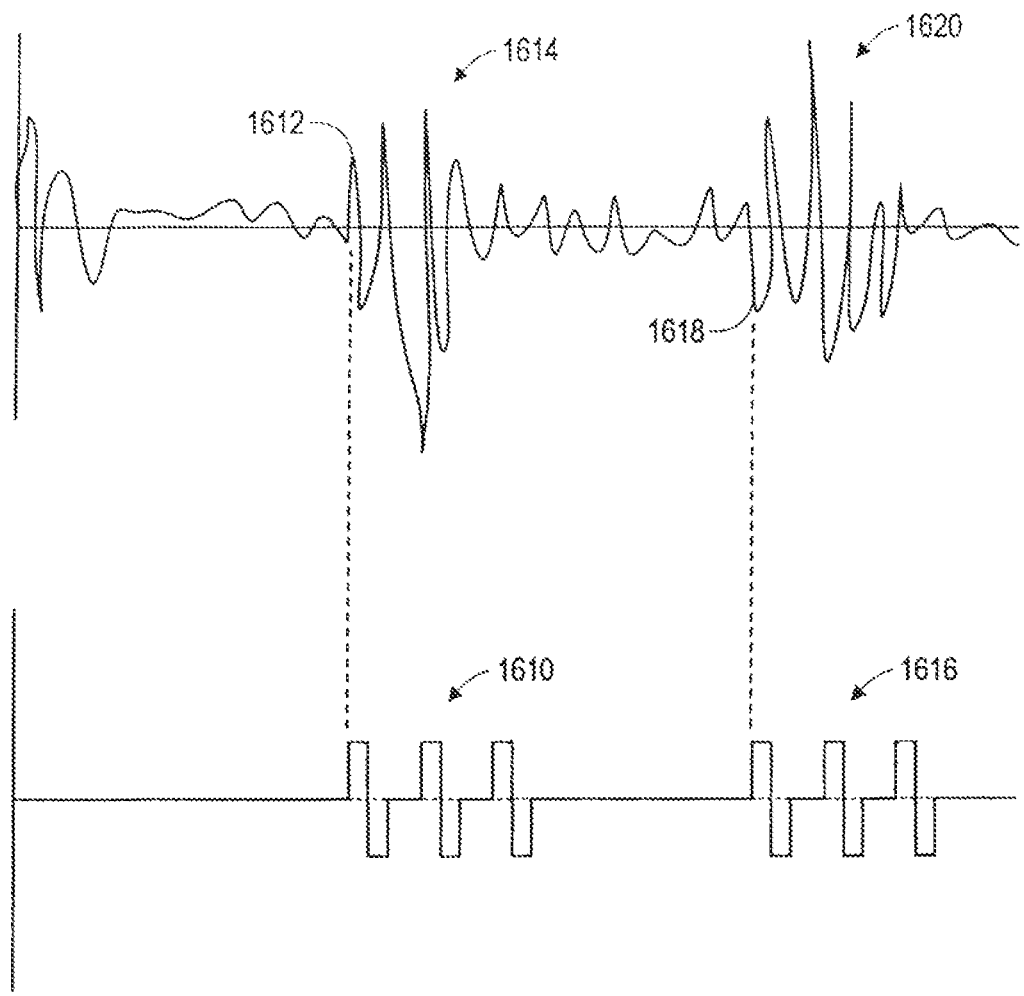
FIG. 16 illustrates correlating the application of electrical stimulation therapy with observed tremor oscillations with a system according to the invention.

As generally described above and as considered in greater detail below, it may be clinically advantageous and particularly effective to synchronize bursts of electrical stimulation treatment with the oscillations of tremor. This can be accomplished with either responsive electrical stimulation or programmed electrical stimulation. This synchronization is illustrated in FIG. 16.

As illustrated, the beginning of a first stimulation burst 1610 is synchronized with a first early identifiable feature 1612 of a first tremor burst 1614. At this time, the abnormal neurological activity characterizing tremor is at its peak. Similarly, the beginning of a second stimulation burst 1616 (immediately following the first stimulation burst 1610) is synchronized with a second early identifiable feature 1618 of a second tremor burst 1620. The first early identifiable feature 1612 and the second early identifiable feature 1618 are advantageously identified in a neurostimulator 110 according to the invention by the detection methods described in detail herein. In particular, the threshold method (FIG. 8) and the frequency/phase method (FIG. 9) can be used to quickly identify activity of high magnitude in a particular frequency band. Alternatively, half wave detection (FIG. 11) can be calibrated to identify particularly large qualified half waves, which would tend to indicate a maximum in the relevant tremor burst, rather than the beginning, The process advantageously used in generating such synchronized treatment bursts is set forth below.

One process for generating a synchronized treatment waveform is illustrated in detail in FIG. 17. Initially, a time synchronization point is identified (step 1710). As described above, this is generally accomplished by identifying a specific half wave of interest and establishing the end point of that half wave as a reference point for the synchronization point (though other reference points are also possible, based on processing windows, real time, and other timers accessible by a neurostimulator according to the invention). The process of identifying a time synchronization point is illustrated in detail in FIG. 18 and will be described below. The synchronization point is used by the CPU 432 to schedule therapy application (step 1712) by setting up a specific timer interrupt according to the clock supply 438 (FIG. 4). A therapy pattern template (for example, a single pulse, a burst of pulses, or some other waveform) is then selected and associated with the schedule (step 1714). In the disclosed embodiment of the invention, one or more possible therapy templates are stored in the memory subsystem 431 and are made accessible to the CPU 432 and the stimulation subsystem 424. These templates, in an embodiment of the invention, represent one or more of the available stimulation waveforms, such as the ones illustrated in FIG. 14. It should be noted, however, that if selection of a desired template from a plurality of templates is not an aspect of the particular adaptive stimulation employed in an embodiment of the invention, then selection of a template (step 1714) can be performed before the synchronization point is identified (step 1710) or the therapy application is scheduled (step 1712); template selection in such a circumstance does not need to be in a time-critical processing path.

It should be noted that the synchronization point may be obtained from substantially any input channel of a neurostimulator according to the invention. To synchronize stimulation to a neurologically significant input signal, it is generally most effective to use the same input channel for event detection, synchronization, and stimulation. However, to achieve intentional desynchronization or other alteration according to the invention, it may be preferable to derive the synchronization information from a separate channel, which is more likely to have characteristics that are substantially independent from and unaffected by a channel used for detection, stimulation, or transformation of a therapy template. The synchronization point may further be obtained or derived from some other source of information less directly associated with or even unrelated to input channels, such as the clock supply 438 (FIG. 4); this would also tend to achieve variability with respect to neurological activity.

In an alternative embodiment of the invention, three separate channels may be used for event detection, synchronization and extraction of parameters for therapy template transformation, and stimulation. And in a further embodiment, four separate channels may be used for event detection, synchronization, extraction of parameters for therapy template transformation, and stimulation. It is particularly advantageous to be able to provide as much configuration flexibility as possible for varying patient clinical needs.

Although it is generally considered advantageous to be able to modify a single therapy pattern template via characteristics of a measured electrographic signal, it should be observed that in an embodiment of the invention, one aspect of the waveform generation process might be to select a desired template from a collection of multiple templates based on signal characteristic.

A stimulation waveform is then generated (step 1716) according to the selected therapy template and any desired parameters identified in the synchronization point. Data representative of the actual stimulation waveform, as generated and based upon the therapy template and the parameters of the synchronization point, are stored in the memory subsystem 431 for access by the stimulation subsystem 424.

To generate the stimulation waveform according to the selected therapy template and any desirable characteristics extracted from the synchronization point, as indicated in step 1716, a system or method according to the invention is capable of transforming the therapy template in various ways. For example, as described above, the time of the synchronization point is generally used to schedule the delivery of the stimulation waveform. In an alternative embodiment of the invention, the waveform is generated according to not only time synchronization information, but also according to other aspects of the synchronization point.

For example, if the synchronization point represents a qualified half wave, the time, amplitude, and duration of the qualified half wave and the interval between qualified half waves can be used to select or alter the polarity or amplitude of one or more pulses in the stimulation waveform or the therapy template as a whole; to govern the frequency, inter-pulse interval, or pulse width of the stimulation waveform if the desired therapy template is a burst of pulses or some other repeating pattern; or to choose one of a set of possible therapy templates by mapping the desired characteristic of the synchronization point onto a look-up table of therapy templates.

It should be noted that for purposes of increased variation according to the invention, it is not necessary to map electrographic signal characteristics to their analogous counterparts in the stimulation waveform. For example, it may be appropriate in certain circumstances to cause the amplitude of a qualified half wave to modify the duration of a stimulation waveform, or for a qualified half wave duration to specify the maximum amplitude in a burst of pulses. Preferably, a neurostimulator according to the invention is programmable to accomplish whatever form or combination of adaptive stimulation characteristics is found to be advantageous in a particular clinical setting.

In a maximally flexible embodiment of the invention, after each pulse or waveform segment is delivered, the remaining portion of a therapy plan can be revised, resynchronized, retransformed, or otherwise altered in a manner similar to that set forth in FIG. 17 and described below. In particular, it would be advantageous, if desired, to be able to identify a new synchronization point (step 1710) and reschedule therapy (step 1712), thereby allowing each pulse or segment of a stimulation waveform to be individually synchronized, correlated, or otherwise altered with respect to a sensed signal. It may also be advantageous in some circumstances to be able to select a new therapy pattern template (step 1714) or regenerate the therapy waveform (step 1716), or both, according to newly measured characteristics of an input electrographic waveform on any desired channel of the neurostimulator device 110.

In an embodiment of the invention, to achieve variation in stimulation timing, it may be possible to synchronize the delivery of stimulation to events other than a synchronization point (step 1710) that corresponds to some characteristic or feature of an electrographic signal. For example, it may be desirable to synchronize to timer interrupts generated by the clock supply 438 of the neurostimulator device 110, or to any other event or time ascertainable by a subsystem of the neurostimulator device 110.

As described above, the therapy application process of the invention preferably is able to operate in parallel with other operations performed by the implantable neurostimulator device 110 (FIG. 1).

Figure 18:
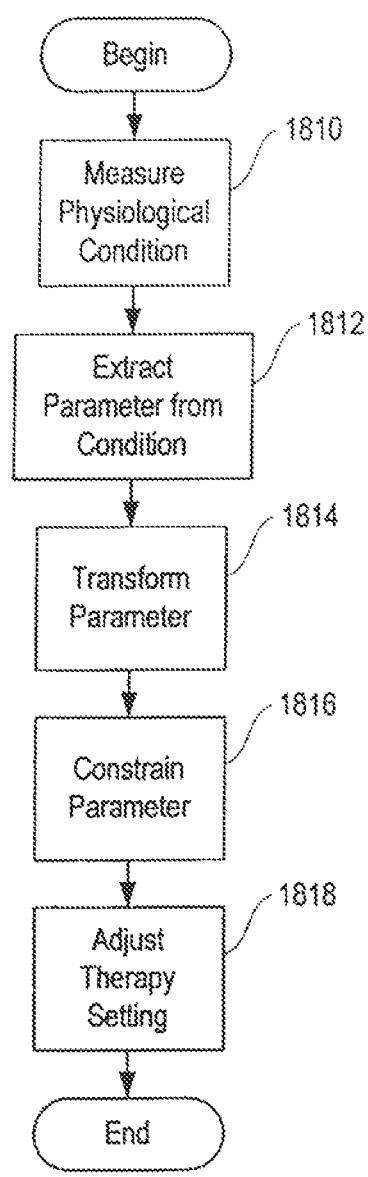
FIG. 18 is a flow chart illustrating a process performed in adjusting electrical stimulation therapy parameters according to a detected neurological event.

As generally described above, the method used to identify a synchronization point in an embodiment of the invention is shown in detail in FIG. 18. When a neurological event is detected or the application of adaptive or synchronized stimulation is deemed desirable, the most recent measurement of a physiological condition (e.g., a half wave extracted from an EEG signal, an EMG area measurement, etc.) is identified (step 1810), and a desired parameter (namely one or more of the time stamp, duration, amplitude, or possibly other parameters related to the measurement) is extracted (step 1812). The extracted parameter is then transformed as desired (step 1814), either linearly or nonlinearly. For example, the extracted parameter can be transformed linearly in one advantageous embodiment by multiplying it by a fixed or variable scale factor and adding a fixed or variable offset. In an embodiment of the invention, stimulation can be approximately synchronized to the analyzed EEG waveform by scheduling a stimulation pulse to occur after the end of the most recent qualified half wave (of sufficient amplitude and duration to suggest tremor) by a fixed delay between approximately 0 and 1000 milliseconds, a percentage of the delay between 0 and 100% of the measured interval between the 3-5 Hz tremor oscillations, or a combination of fixed and interval-dependent delays. In the disclosed embodiment of the invention, the measured interval between waves is preferably calculated as the time delay between successive qualified half waves, as stored in a FIFO queue.

If desired, the parameters extracted from recent qualified half waves, as transformed, are constrained by minimum and maximum values (step 1816). Preferably, the adaptive interval-based delay described above is constrained by programmable minimum and maximum values between about 0 and 1000 milliseconds.

For a burst of pulses, not only can the timing of the first pulse be governed by a fixed or interval-dependent delay, but the inter-pulse interval can also be controlled in a similar manner. For example, either the duration or the interval of qualified half waves in the FIFO queue can be used to control the inter-pulse interval, and qualified half wave amplitudes can be used to modify the amplitudes of subsequent pulses, or of the burst as a whole. Generally, controlling the parameters of each pulse of a burst separately would be advantageously accomplished by scheduling each pulse in the burst as a separate stimulation event, and causing the methods of the invention to extract information from the electrographic signal and generate an adaptive pulse for each separately scheduled stimulation event.

Many possible uses of the parameters described above are possible. To provide decorrelation, rather than synchronization, as discussed above, it is possible to map qualified half wave duration or interval to stimulation amplitude, or qualified half wave amplitude to stimulation timing or frequency, for example. In other detection schemes, such as those reliant on waveform line length or area, as described above, parameters related to those measurements can also be used to provide a measure of variability to a stimulation signal.

Similar waveform shaping and timing considerations can be applied to other stimulation waveforms, as well. To provide but one example, the frequency of sinusoidal stimulation may be derived from the half wave interval. Other possibilities consistent with the invention should be apparent.

It should be observed that while the foregoing detailed description of various embodiments of the present invention is set forth in some detail, the invention is not limited to those details and an implantable neurostimulator or other device made according to the invention can differ from the disclosed embodiments in numerous ways. In particular, it will be appreciated that embodiments of the present invention may be employed in many different applications to detect and treat movement disorders and other conditions via responsive electrical stimulation in a patient's brain. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. An implantable neurostimulator for treating a patient experiencing a movement disorder comprising:
    a sensor interface for receiving a first signal from a first sensor configured to sense electrical activity of the brain and a second signal from a second sensor configured to sense motion of the patient;
    a detection subsystem for analyzing the first signal and the second signal, the detection subsystem configured to:
        measure a frequency of the first signal and a frequency of the second signal,
        calculate a frequency offset corresponding to the difference between the frequency of the first signal and the frequency of the second signal,
        compare the frequency offset to a frequency criterion,
        measure a phase of the first signal and a phase of the second signal;
        calculate a phase offset corresponding to the difference between the phase of the first signal and the phase of the second signal,
        compare the phase offset to a phase criterion, and
        detect a tremor event when both the frequency criterion and the threshold criterion are satisfied; and
    a stimulation subsystem configured to deliver a treatment to the patient from the neurostimulator.

2. The implantable neurostimulator of claim 1, wherein the frequency criterion is an offset value and the frequency criterion is satisfied when the frequency offset is within a specified range of the value.

3. The implantable neurostimulator of claim 2, wherein the offset value is near zero.

4. The implantable neurostimulator of claim 1, wherein the phase criterion is an offset constant and the phase criterion is satisfied when the phase offset is within a specified range of the offset constant.

5. The implantable neurostimulator of claim 4, wherein the offset constant is a patient-specific constant.

6. The implantable neurostimulator of claim 1, wherein in order to measure a phase of the first signal and a phase of the second signal, the detection subsystem is further configured to:
    determine a first time at which a first landmark of a waveform representative of the first signal occurs; and
    determine a second time at which a second landmark of a waveform representative of the second signal occurs, the second landmark being the same type of landmark as the first landmark.

7. The implantable neurostimulator of claim 6, wherein the waveform representative of the first signal comprises a plurality of peaks and the first landmark corresponds to the largest peak of the plurality of peaks, and the waveform representative of the second signal comprises a plurality of peaks and the second landmark correspond to the largest peak of the plurality of peaks.

8. The implantable neurostimulator of claim 1, wherein the first and second signal are continuously received by the sensor interface and continuously analyzed by the detection subsystem.

9. The implantable neurostimulator of claim 8, wherein the stimulation subsystem is configured to:
    deliver treatment for so long as the tremor event is detected; and
    cease delivery of the treatment when the tremor event is no longer detected.

10. A method for treating a movement disorder in a human patient with an implantable neurostimulator comprising:
    receiving a first signal from a first sensor configured to sense electrical activity of the brain;
    receiving a second signal from a second sensor configured to sense motion of the patient;
    analyzing the first signal and the second signal to determine whether a tremor characteristic of an episode of the movement disorder is occurring, wherein analyzing the first and second signals comprises:
        measuring a frequency of the first signal and a frequency of the second signal,
        calculating a frequency offset corresponding to the difference between the frequency of the first signal and the frequency of the second signal,
        comparing the frequency offset to a frequency criterion,
        measuring a phase of the first signal and a phase of the second signal;
        calculating a phase offset corresponding to the difference between the phase of the first signal and the phase of the second signal,
        comparing the phase offset to a phase criterion, and
        detecting a tremor event when both the frequency criterion and the threshold criterion are satisfied; and
    delivering a treatment to the patient from the neurostimulator.

11. The method of claim 10, wherein the frequency criterion is an offset value and the frequency criterion is satisfied when the frequency offset is within a specified range of the offset value.

12. The method of claim 11, wherein the offset value is near zero.

13. The method of claim 10, wherein the phase criterion is an offset constant and the phase criterion is satisfied when the phase offset is within a specified range of the offset constant.

14. The method of claim 13, wherein the offset constant is a patient-specific constant.

15. The method of claim 10, wherein measuring a phase of the first signal and a phase of the second signal comprises:
    determining a first time at which a first landmark of a waveform representative of the first signal occurs; and determining a second time at which a second landmark of a waveform representative of the second signal occurs, the second landmark being the same type of landmark as the first landmark.

16. The method of claim 10, wherein the waveform representative of the first signal comprises a plurality of peaks and the first landmark corresponds to the largest peak of the plurality of peaks, and the waveform representative of the second signal comprises a plurality of peaks and the second landmark correspond to the largest peak of the plurality of peaks.

17. The method of claim 10, wherein the first and second signal are continuously received and analyzed.

18. The method of claim 17, wherein the treatment is delivered for so long as the tremor event is detected, the method further comprising ceasing delivery of the treatment when the tremor event is no longer detected.

* * * * *

UNITED STATES PATENT AND TRADEMARK OFFICE
CERTIFICATE OF CORRECTION

PATENT NO. : 9,126,042 B2
APPLICATION NO. : 14/484701
DATED : September 8, 2015
INVENTOR(S) : Thomas K. Tcheng et al.

It is certified that error appears in the above-identified patent and that said Letters Patent is hereby corrected as shown below:

In the Specification

Column 1, lines 10-12 read:

This is a divisional of U.S. Ser. No. 14/059,090, filed Oct. 21, 2013, which is a continuation of U.S. Ser. No. 12/881,143, filed Sep. 13, 2010, now U.S. Pat. No. 8,594,795, which is a continuation of U.S. Ser. No. 11/517,783, filed Sep. 8, 2006, now U.S. Pat. No. 7,813,802, which is a continuation of U.S. Ser. No. 10/072,669, filed Feb. 2, 2002, now U.S. Pat. No. 7,110,820, each of which is hereby incorporated by reference in its entirety.

Column 1, lines 10-12 should read:

This is a divisional of U.S. Ser. No. 14/059,090, filed Oct. 21, 2013, which is a continuation of U.S. Ser. No. 12/881,143, filed Sep. 13, 2010, now U.S. Pat. No. 8,594,795, which is a continuation of U.S. Ser. No. 11/517,783, filed Sep. 8, 2006, now U.S. Pat. No. 7,813,802, which is a continuation of U.S. Ser. No. 10/072,669, filed Feb. 5, 2002, now U.S. Pat. No. 7,110,820, each of which is hereby incorporated by reference in its entirety.

Signed and Sealed this
Ninth Day of August, 2016

Michelle K. Lee
*Director of the United States Patent and Trademark Office*